(12) United States Patent
Masuno et al.

(10) Patent No.: US 11,905,362 B2
(45) Date of Patent: Feb. 20, 2024

(54) POLYMERS AND METHODS OF PRODUCING THEREOF

(71) Applicant: Origin Materials Operating, Inc., Sacramento, CA (US)

(72) Inventors: Makoto Nathanael Masuno, Elk Grove, CA (US); Dimitri A. Hirsch-Weil, West Sacramento, CA (US); Alexander Crewe-Read Millar, West Sacramento, CA (US); Alexander Yeuham Joh, West Sacramento, CA (US)

(73) Assignee: Origin Materials Operating, Inc., West Sacramento, CA (US)

( * ) Notice: Subject to any disclaimer, the term of this patent is extended or adjusted under 35 U.S.C. 154(b) by 0 days.

(21) Appl. No.: 17/561,072

(22) Filed: Dec. 23, 2021

(65) Prior Publication Data

US 2022/0372213 A1 Nov. 24, 2022

Related U.S. Application Data

(63) Continuation of application No. 16/333,870, filed as application No. PCT/US2017/051935 on Sep. 15, 2017, now abandoned.

(60) Provisional application No. 62/396,076, filed on Sep. 16, 2016.

(51) Int. Cl.
| | |
|---|---|
| *C08G 63/16* | (2006.01) |
| *C07D 307/68* | (2006.01) |
| *C08K 5/00* | (2006.01) |
| *C08K 5/524* | (2006.01) |
| *B01J 31/22* | (2006.01) |
| *C08G 63/181* | (2006.01) |
| *C08K 5/1535* | (2006.01) |

(52) U.S. Cl.
CPC ........ *C08G 63/181* (2013.01); *B01J 31/2273* (2013.01); *C07D 307/68* (2013.01); *C08G 63/16* (2013.01); *C08K 5/005* (2013.01); *C08K 5/1535* (2013.01); *C08K 5/524* (2013.01)

(58) Field of Classification Search
CPC ...... C08G 63/16; C08G 63/80; C08G 63/181; C07D 307/68; C08K 5/005; C08K 5/524; C08K 5/1535; B01J 31/2273
See application file for complete search history.

(56) References Cited

U.S. PATENT DOCUMENTS

| 2,551,731 | A | 5/1951 | Napier et al. |
|---|---|---|---|
| 8,143,355 | B2 | 3/2012 | Matsuda et al. |
| 9,567,431 | B2 | 2/2017 | Sipos |
| 2009/0018264 | A1 | 1/2009 | Fuseya |
| 2009/0124763 | A1 | 5/2009 | Matsuda et al. |
| 2011/0282020 | A1 | 11/2011 | Sipos |
| 2012/0220507 | A1 | 8/2012 | Grass et al. |
| 2013/0095263 | A1 | 4/2013 | Carman et al. |
| 2013/0095269 | A1 | 4/2013 | Carman et al. |
| 2013/0095270 | A1 | 4/2013 | Carman et al. |
| 2013/0171397 | A1 | 7/2013 | Ghosh et al. |
| 2013/0345453 | A1 | 12/2013 | Sipos et al. |
| 2014/0194633 | A1 | 7/2014 | Mikochik et al. |
| 2014/0336349 | A1* | 11/2014 | Sipos ............... C08G 63/80 528/306 |
| 2015/0047251 | A1 | 2/2015 | Mikochik et al. |
| 2016/0145415 | A1 | 5/2016 | Chaudhary |
| 2018/0265629 | A1 | 9/2018 | Bissell et al. |
| 2019/0202977 | A1 | 7/2019 | Masuno et al. |

FOREIGN PATENT DOCUMENTS

| CN | 103073704 A | 5/2013 |
|---|---|---|
| CN | 104024301 A | 9/2014 |
| CN | 104379631 A | 2/2015 |
| EP | 1948709 B1 | 5/2013 |
| EP | 2445855 B2 | 6/2018 |
| GB | 621971 A | 4/1949 |
| JP | 200850498 A | 3/2008 |
| JP | 200875068 A | 4/2008 |
| JP | 2008120881 A | 5/2008 |
| JP | 2008291243 A | 12/2008 |
| JP | 2008291244 A | 12/2008 |
| JP | 2009062465 A | 3/2009 |
| JP | 2009179740 A | 8/2009 |
| JP | 2009215467 A | 9/2009 |
| WO | WO-2004060987 A2 | 7/2004 |
| WO | WO-2007052847 A1 | 5/2007 |
| WO | WO-2009104478 A1 | 8/2009 |
| WO | WO-2009104479 A1 | 8/2009 |

(Continued)

OTHER PUBLICATIONS

Stefan Naumann and Andrew P Dove, N-Heterocyclic carbenes for metal-free polymerization catalysis: an update,Polym Int 2016; 65: 16-27. (Year: 2015).*

(Continued)

*Primary Examiner* — Bijan Ahvazi

(74) *Attorney, Agent, or Firm* — Nixon & Vanderhye, P.C.

(57) ABSTRACT

Provided herein are methods of producing polymers from furan and optionally diol compounds, using an organocatalyst. A polymer composition comprising a polymer prepared by the method is contemplated. Provided herein are also polymer compositions, such as poly(alkylene-2,5-furandicarboxylate). In some embodiments, polymer compositions have any one of the characteristics discussed herein, or any combinations thereof.

22 Claims, No Drawings

(56) References Cited

FOREIGN PATENT DOCUMENTS

| | | | |
|---|---|---|---|
| WO | WO-2009104780 | A1 | 8/2009 |
| WO | WO-2010077133 | A1 | 7/2010 |
| WO | WO-2012091573 | A9 | 6/2013 |
| WO | WO-2014193634 | A1 | 12/2014 |
| WO | WO-2015137804 | A1 | 9/2015 |
| WO | WO-2015137807 | A1 | 9/2015 |
| WO | WO-2015142181 | A1 | 9/2015 |
| WO | WO-2018053372 | A1 | 3/2018 |

OTHER PUBLICATIONS

Al-Sabagh et al., (2016). "Greener Routes for Recycling of Polyethylene Terephthalate," Egyptian Journal of Petroleum, 25:53-64.

Amyes et al., (2004). "Formation and Stability of N-Heterocyclic Carbenes in Water: The Carbon Acid pKa of Imidazolium Cations in Aqueous Solution," The Journal of Organic Chemistry, 126(13):4366-4374.

Bourissou et al., (2000). "Stable Carbenes," Chemical Reviews, 100(1):39-91.

Burgess et al., (2014). Chain Mobility, Thermal, and Mechanical Properties of Poly(Ethylene Furanoate) Compared to Poly(Ethylene Terephthalate), Macromolecules, 47:1383-1391.

Burgess et al., (2015). "Carbon Dioxide Sorption and Transport in Amorphous Poly(Ethylene Furanoate)," Macromolecules, 48:2184-2193.

Delidovich et al., (2016). "Alternative Monomers Based on Lignocellulose and Their Use for Polymer Production," Chemical Reviews, 116:1540-1599.

Di Fiore et al., (1993). "Influence of the antimony catalyst remnants on the melt crystallization of PET," Journal of Applied Polymer Science, 48(11):1997-2001.

Eastman, (2007). "N-Heterocyclic Carbenes (NHCs)," Baran Lab, 18 pages.

Enders et al., (2007). "Organocatalysis by N-Heterocyclic Carbenes," Chemical Reviews, 107(12):5606-5655.

Fèvre et al., (2013). "N-Heterocyclic Carbenes (NHCs) as Organocatalysts and Structural Components in Metal-Free Polymer Synthesis," Chemical Society Reviews, 42:2142-2172.

Final Office Action received for U.S. Appl. No. 15/760,973, dated Nov. 4, 2019, 12 pages.

Flanigan et al., (2015). "Organocatalytic Reactions Enabled by N-Heterocyclic Carbenes," Chemical Reviews, 115:9307-9387.

Gandini et al., (2009). "The Furan Counterpart of Poly(ethylene terephthalate): An Alternative Material Based on Renewable Resources," Journal of Polymer Science: Part A: Polymer Chemistry, 47:295-298.

Gomes et al., (2011). "Synthesis and Characterization of Poly(2,5-Furan Dicarboxylate)s Based on a Variety of Diols," Journal of Polymer Science Part A: Polymer Chemistry, 49:3759-3768.

Gopalakrishnan et al., (2014). "Synthesis and Characterization of Bio-based Furanic Polyesters," Journal of Polymer Research, 21(340):1-9.

Gruter et al., (2012). "Accelerating Research into Bio-Based FDCA-Polyesters by Using Small Scale Parallel Film Reactors," Combinatorial Chemistry & High Throughput Screening, 15(2):180-188.

Heertjes et al., (1974). "Polycondensation Products of 2,5-Furandicarboxylic Acid," Delft Progress Report Series A: Chemistry and Physics, Chemistry and Physical Engineering, 1:59-63.

Hong et al., (2016). "Proton-Transfer Polymerization by N-Heterocyclic Carbenes: Monomer and Catalyst Scopes and Mechanism for Converting Dimethacrylates into Unsaturated Polyesters," Journal of the American Chemical Society, 138:2021-2035.

International Preliminary Report on Patentability received for PCT Patent Application No. PCT/US2016/052344, dated Mar. 29, 2018, 7 pages.

International Preliminary Report on Patentability received for PCT Patent Application No. PCT/US2017/051935, dated Mar. 28, 2019, 8 pages.

International Search Report and Written Opinion Received for PCT Application No. PCT/US2016/052344, dated Dec. 16, 2016, 9 pages.

International Search Report and Written Opinion received for PCT Patent Application No. PCT/US2017/051935, dated Dec. 1, 2017, 10 pages.

Izunobi et al., (2011). "Polymer Molecular Weight Analysis by 1H NMR Spectroscopy," Journal of Chemical Education, 88:1098-1104.

Jiang et al., (2012). "A Biocatalytic Approach Towards Sustainable Furanic-Aliphatic Polyesters," Polymer Chemistry, 6:5198-5211.

Jiang et al., (2015). "A Series of Furan-Aromatic Polyesters Synthesized via Direct Esterification Method Based on Renewable Resources," Journal of Polymer Science Part A: Polymer Chemistry, 50:1026-1036.

Kamber et al., (2010). "The Depolymerization of Poly(Ethylene Terephthalate) (PET) Using N-Heterocyclic Carbenes from Ionic Liquids," Journal of Chemical Education, 87(5):519-521.

Kazaryan et al., (1968). "X-Ray Study of Poly(Ethylene Furan-2,5-Dicarboxylate) Structure," Vysokomolekulârnye Soedineniâ. Seriâ B, 10(4):305-306 (Foreign Language).

Kiesewetter et al., (2010). "Organocatalysis: Opportunities and Challenges for Polymer Synthesis," Macromolecules, 43(5):2093-2107.

Knoop et al., (2013). "High Molecular Weight Poly(ethylene-2,5-furanoate); Critical Aspects in Synthesis and Mechanical Property Determination," Journal of Polymer Science, Part A: Polymer Chemistry, 51:4191-4199.

Lai et al., (2005). "Theoretical Study on the Mechanism of N-Heterocyclic Carbene Catalyzed Transesterification Reactions," Tetrahedron Letters, 46:6265-6270.

Lindner et al., (2014). "Ring-Opening Polymerization and Copolymerization of Propylene Oxide Catalyzed by N-Heterocyclic Carbenes," ChemCatChem, 6:618-625.

Loos et al., (2020). "A Perspective on PEF Synthesis, Properties, and End-Life," Frontiers in Chemistry, 8(585), 18 pages.

Ma et al., (2012). "The Copolymerization Reactivity of Diols with 2,5-Furandicarboxylic Acid for Furan-based Copolyester Materials," Journal of Materials Chemistry, 22:3457-3461.

Mao et al., (2016). "The Crystal Structure of Poly(ethylene furanoate)," Polymer, 102, 20 pages.

Massey et al., (2012). "Proton Transfer Reactions of Triazol-3-ylidenes: Kinetic Acidities and Carbon Acid pKa Values for Twenty Triazolium Salts in Aqueous Solution," Journal of the American Chemical Society, 134:20421-20432.

Matos et al., (2014). "A New Generation of Furanic Copolyesters with Enhanced Degradability: Poly(Ethylene 2,5-Furandicarboxylate)-Co-Poly(Lactic Acid) Copolyesters," Macromolecular Chemistry and Physics, 215:2175-2184.

Medvedeva et al., (1963). "Preparation of Mixed Polyesters of Ethylene Glycol with 2,5-Furandicarboxylic and Terephthalic Acids," Plasticheskie Massy, 2:14-15 (Foreign Language).

Medvedeva et al., (1968). "2-Butyne-1,4-Diol and 2,2,3,3-Tetrachloro-1,4-Butanediol Copolyesters," Plasticheskie Massy, 9:26-27 (Foreign Language).

Medvedeva et al., (1971). "Heat-Resistant Adhesives for a Poly(Ethylene Terephthalate) Film," Plasticheskie Massy, 7:67-68 (Foreign Language).

Medvedeva et al., (1971). "Orientation of Films From Furan-Containing Copolymers," Plasticheskie Massy, 8:32-33 (Foreign Language).

Medvedeva et al., (1973). "Modified Poly(Ethylene Terephthalate)," Plasticheskie Massy, 4:39-40 (Foreign Language).

Mespouille et al., (2014). "Implementation of Metal-Free Ring-Opening Polymerization in the Preparation of Aliphatic Polycarbonate Materials," Progress in Polymer Science, 39:1144-1164.

Mihailov et al., (1968). "Preparation and Three-Dimensional Polymerization of Polyester Methacrylates," Journal of Polymer Science: Part C, 16:3811-3820.

Morales-Huerta et al., (2016). "Poly(Alkylene 2,5-Furandicarboxylate)s (PEF and PBF) by Ring Opening Polymerization," Polymer, 87:148-158.

(56) References Cited

OTHER PUBLICATIONS

Naumann et al., (2015). "N-Heterocyclic Carbenes as Organocatalysts for Polymerizations: Trends and Frontiers," Polymer Chemistry, 6:3185-3200.

Non-Final Office Action received for U.S. Appl. No. 15/760,973, dated Apr. 19, 2019, 9 pages.

Noonan et al., (2008). "Nucleophilic Carbene-Catalysed Oxidative Esterification Reactions," Tetrahedron Letters, 49:4003-4006.

Nyce et al., (2002). "Expanding the Catalytic Activity of Nucleophilic N-Heterocyclic Carbenes for Transesterification Reactions," Organic Letters, 4(21):1-10.

Nyce et al., (2003). "In Situ Generation of Carbenes: A General and Versatile Platform for Organocatalytic Living Polymerization," The Journal of Organic Chemistry, 125(10):3046-3056.

Otera, (1993). "Transesterification," Chemical Reviews, 93(4):1449-1470.

Otto et al., (2001). "Enhanced PET Production through New Heavy Metal-Free Catalyst Systems," Chemical Fibers International, 51(3):188-189.

Papageorgiou et al., (2014). "Evaluation of Polyesters from Renewable Resources as Alternatives to the Current Fossil-based Polymers. Phase Transitions of Poly(Butylene 2,5-Furan-Dicarboxylate), " Polymer, 55:3846-3858.

Papageorgiou et al., (2014). "Synthesis of Poly(Ethylene Furandicarboxylate) Polyester using Monomers Derived from Renewable Resources: Thermal Behavior Comparison with PET and PEN," Physical Chemistry Chemical Physics, 16:7946-7958.

Papageorgiou et al., (2015). "Synthesis of the Bio-Based Polyester Poly(Propylene 2,5-Furan Dicarboxylate). Comparison of Thermal Behavior and Solid State Structure with its Terephthalate and Naphthalate Homologues," Polymer, 62:28-38.

Papageorgiou et al., (2016). "Production of Bio-based 2,5-Furan Dicarboxylate Polyesters: Recent Progress and Critical Aspects in their Synthesis and Thermal Properties," European Polymer Journal, 83:202-229.

Pignataro et al., (2009). "Unusual Mechanistic Course of Some NHC-Mediated Transesterifications," Organic Letters, 11(7):1643-1646.

Pinaud et al., (2011). "Poly(N-heterocyclic-carbene)s and their CO2 Adducts as Recyclable Polymer-Supported Organocatalysts for Benzoin Condensation and Transesterification Reactions," Macromolecules, 44:1900-1908.

Qu et al., (2019). "A Brønsted Acidic Ionic Liquid as an Efficient and Selective Catalyst System for Bioderived High Molecular Weight Poly(ethylene 2,5-furandicarboxylate)," ChemSusChem, 12(22):4927-4935.

Search Report received for Chinese Patent Application No. 2016800667347 completed on Jul. 21, 2021, 4 pages.

Sentman et al., (2005). "Silver(I)-Carbene Complexes/Ionic Liquids: Novel N-Heterocyclic Carbene Delivery Agents for Organocatalytic Transformations," The Journal of Organic Chemistry, 70(6):2391-2393.

Smith, (2015). "B.Bio-Based Sources for Terephthalic Acid," Green Polymer Chemistry: Biobased Materials and Biocatalysis, Chapter 27, pp. 453-469.

Sousa et al., (2013). "New Copolyesters Derived from Terephthalic and 2,5-Furandicarboxylic Acids: A Step Forward in the Development of Biobased Polyesters," Polymer, 54:513-519.

Sousa et al., (2015). "Biobased Polyesters and Other Polymers from 2,5-Furandicarboxylic Acid: A Tribute to Furan Excellency," Polymer Chemistry, 6:5961-5983.

Tsanaktsis et al., (2015). "Crystallization and Polymorphism of Poly(Ethylene Furanoate)," Crystal Growth & Design, 15:5505-5512.

Tsanaktsis et al., (2015). "Thermal Degradation Kinetics and Decomposition Mechanism of Polyesters based on 2,5-Furandicarboxylic Acid and Low Molecular Weight Aliphatic Diols," Journal of Analytical and Applied Pyrolysis, 112:369-378.

Wu et al., (2014). "Biobased Poly(Butylene 2,5-Furandicarboxylate) and Poly(Butylene Adipate-Co-Butylene 2,5-Furandicarboxylate)s: From Synthesis using Highly Purified 2,5-Furandicarboxylic Acid to Thermo-Mechanical Properties," Polymer, 55:3648-3655.

Wu et al., (2017). "DBU-catalyzed biobased poly(ethylene 2,5-furandicarboxylate) polyester with rapid melt crystallization: synthesis, crystallization kinetics and melting behavior," RSC Adv., 6:101578-101586.

Zeng et al., (2009). "Separation, Recovery and Reuse of N-Heterocyclic Carbene Catalysts in Transesterification Reactions," Chemical Communications, pp. 6249-6251.

Zhu et al., (2013). "Poly(Butylene 2,5-Furan Dicarboxylate), a Biobased Alternative to PBT: Synthesis, Physical Properties, and Crystal Structure," Macromolecules, 43:796-804.

Final Office Action received for U.S. Appl. No. 16/333,870, dated Oct. 9, 2020, 13 pages.

Non-Final Office Action received for U.S. Appl. No. 16/333,870, dated Apr. 20, 2020, 14 pages.

Non-Final Office Action received for U.S. Appl. No. 16/333,870, dated Jun. 25, 2021, 13 pages.

\* cited by examiner

POLYMERS AND METHODS OF PRODUCING THEREOF

CROSS-REFERENCE TO RELATED APPLICATION

This application is a continuation of U.S. application Ser. No. 16/333,870, filed on Mar. 15, 2019, which is a national phase application under 35 U.S.C. 371 of International Application No. PCT/US2017/051935, filed internationally on Sep. 15, 2017, which claims the benefit of U.S. Provisional Application No. 62/396,076, filed on Sep. 16, 2016, which are hereby incorporated by reference in their entireties.

FIELD

The present disclosure relates generally to the production of furan polymer compositions, and more specifically to the production of furan polyesters from 2,5-furandicarboxylic acid or 2,5-tetrahydrofurandicarboxylic acids or esters.

BACKGROUND

Polyesters are commonly used to produce, for example, fabrics for clothing and home furnishings, as well as bottles. Various methods are known in the art to produce polyesters. Such methods known in the art traditionally involve polymerization using transition metal catalysts. However, the polyester produced has residual transition metal which can interfere with downstream products, or which is desired to be removed from downstream products. For example, there is public concern regarding the presence of metals, such as residual transition metals from catalyst, in plastic bottles made from polyesters. The color of the resulting polyester can also be an important factor in the use of the material.

Thus, there is a need for alternative methods to produce polyesters with a lower transition metal content, and low color content. Further, what is desired in the art are methods to produce polyesters from renewable sources.

BRIEF SUMMARY

In some aspects, provided is a composition comprising a polymer with a polymer backbone made up of a furan carboxylate moiety or a tetrahydrofuran carboxylate moiety. In some variations, the polymer backbone is made up of an optionally substituted 2,5-furandicarboxylate moiety or an optionally substituted 2,5-tetrahydrofurandicarboxylate moiety. In certain variations, the polymer is poly(alkylene-2,5-furandicarboxylate) or poly(alkylene-2,5-tetrahydrofurandicarboxylate). In one variation, the polymer is poly(ethylene-2,5-furandicarboxylate), also known in the art as "PEF".

In some embodiments, polymer compositions have any one of the characteristics discussed herein, or any combinations thereof. Also contemplated and provided herein are some embodiments of polymer compositions consisting of or consisting substantially of one of the characteristics discussed herein, or any combinations thereof.

The polymer compositions, in some embodiments, have a low metal content, low color and high molecular weight. In some embodiments, the polymer compositions comprise a residue from the N-heterocyclic carbene of formula (C1):

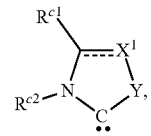

(C1)

and have high molecular weight.

In some variations, the composition is free from metal catalysts. The metal catalysts may include, for example, catalysts typically used to produce the polymer. In some variations, such metal catalysts include transition metals, post-transition metals, metalloids, and/or lanthanoid metals. In some embodiments, the composition has a metal content that does not come from catalysts used to produce the polymer. In one variation of the foregoing, catalysts that may be used to produce the polymer include transesterification catalysts.

In certain variations, the composition is free from metals, including transition metals, post-transition metals, metalloids, and/or lanthanoid metals; provided, however, that alkali metals, alkaline earth metals, and silicon may be present. In one variation, such alkali metals, alkaline earth metals, and silicon may be present in the composition in trace amounts.

In other variations, the composition has a metal content of less than 1 wt %. In one variation of the foregoing, the metal content includes the content of any metals, including any transition metals, post-transition metals, metalloids, and/or lanthanoid metals, but excludes the content of any alkali metals, alkaline earth metals, and silicon.

In some embodiments that may be combined with any of the foregoing variations, a solution of 5 mg/mL of the composition in hexafluoroisopropanol has an absorbance of less than 0.05 at 400 nm.

In yet other embodiments that may be combined with any of the foregoing variations, the composition has a number average molecular weight of at least 10,000 Da.

In another aspect, provided herein is a method of producing a polymer composition, by:

a) combining a furan or a tetrahydrofuran with a diol in the presence of an organocatalyst, wherein:
  the furan or the tetrahydrofuran is optionally substituted furan-2,5-dicarboxylic acid, optionally substituted furan-2,5-dicarboxylic acid dialkyl ester, optionally substituted tetrahydrofuran-2,5-dicarboxylic acid, or optionally substituted tetrahydrofuran-2,5-dicarboxylic acid dialkyl ester; and
  the diol is alkyl, cycloalkyl, heterocycloalkyl, aryl, heteroaryl, or ether,
    wherein the cycloalkyl, heterocycloalkyl, aryl, heteroaryl, or ether is optionally substituted with one or more alkyl groups, and is substituted with two substituents independently selected from the group consisting of —OH and —R$^P$—OH, wherein R$^P$ is alkyl; and
b) esterifying at least a portion of the furan or the tetrahydrofuran with at least a portion of the diol to produce the polymer composition.

In another aspect, provided herein is a method of producing a polymer composition, by:

a) combining a furan or a tetrahydrofuran with a diol in the presence of an organocatalyst, wherein:
  the furan or the tetrahydrofuran is optionally substituted furan-2,5-dicarboxylic acid, optionally substituted furan-2,5-dicarboxylic acid dialkyl ester, optionally substituted tetrahydrofuran-2,5-dicarboxylic acid, or optionally substituted tetrahydrofuran-2,5-dicarboxylic acid dialkyl ester; and the diol is alkyl, cycloalkyl, heterocycloalkyl, aryl, heteroaryl, or ether,
wherein the cycloalkyl, heterocycloalkyl, aryl, heteroaryl, or ether is optionally substituted with one or more alkyl groups, and is substituted with two substituents independently selected from the group consisting of —OH and —R$^P$—OH, wherein R$^P$ is alkyl;

b) esterifying at least a portion of the furan or the tetrahydrofuran with at least a portion of the diol to produce a prepolymer composition; and c) polycondensing at least a portion of the prepolymer composition to produce the polymer composition.

In yet another aspect, provided herein is a method of producing a polymer composition, by:

a) combining a furan or a tetrahydrofuran with a diol in the presence of an organocatalyst, wherein:
the furan or the tetrahydrofuran is optionally substituted furan-2,5-dicarboxylic acid, optionally substituted furan-2,5-dicarboxylic acid dialkyl ester, optionally substituted tetrahydrofuran-2,5-dicarboxylic acid, or optionally substituted tetrahydrofuran-2,5-dicarboxylic acid dialkyl ester; and the diol is alkyl, cycloalkyl, heterocycloalkyl, aryl, heteroaryl, or ether,
wherein the cycloalkyl, heterocycloalkyl, aryl, heteroaryl, or ether is optionally substituted with one or more alkyl groups, and is substituted with two substituents independently selected from the group consisting of —OH and —R$^P$—OH, wherein R$^P$ is alkyl;

b) esterifying at least a portion of the furan or the tetrahydrofuran with at least a portion of the diol to produce a prepolymer composition;

c) polycondensing at least a portion of the prepolymer composition to produce a polymer condensate composition; and d) drying and/or crystallizing the polymer condensate composition to produce the polymer composition.

In some variations of the foregoing methods, the diol is an alkyl diol.

In yet another aspect, provided herein is a method that includes polymerizing a furan or a tetrahydrofuran in the presence of an organocatalyst to produce a poly(alkylene-2,5-furandicarboxylate), a poly(alkylene-2,5-tetrahydrofurandicarboxylate), or a mixture thereof. In some variations, the furan or the tetrahydrofuran is a compound of formula (G):

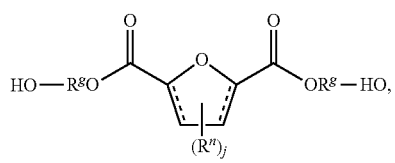

(G)

wherein:
=== is a double bond or a single bond;
j is 2 when === is a double bond, or j is 6 when === is a single bond j;
each R″ is independently H, aromatic or aliphatic; and each R$^g$ is independently aromatic or aliphatic, wherein the R$^g$ is optionally substituted with one or more additional hydroxyl groups.

In other variations of the foregoing methods, the organocatalyst is a non-metal catalyst. In certain variations, the organocatalyst is a non-transition metal catalyst. In certain variations of the methods, the organocatalyst is a nitrogen-containing carbene. In one variation, the organocatalyst is an N-heterocyclic carbene.

In some variations of the foregoing methods, the method is performed at a temperature below about 200° C.

In some variations of the foregoing methods, an antioxidant is used in the method to reduce the color of the composition produced.

In some aspects, provided is a polymer composition produced according to any of the methods described herein. In some variations of the polymer compositions described herein, including produced according to the methods described herein, has less than 0.1 wt % metal. In certain variations, the polymer composition has less than 0.1 wt % of a transition metal. In other variations, the polymer composition has a number average molecular weight of at least 10,000 Da.

The polymer compositions described herein, including produced according to the methods described herein, may be suitable for use in the production of various materials, including fabrics for clothing and home furnishings, as well as bottles. Thus, in some aspects, provided is the use of the polymer compositions described herein in the manufacture of an article. Such articles may include, for example, materials (e.g., fabrics), as well as bottles (e.g., plastic bottles).

In other aspects, provided is a composition comprising the furans or tetrahydrofurans described herein, and the organocatalysts described herein. In some variations, such composition further includes a diol. In other variations, such composition further includes a solvent. In yet other aspects, provided is a composition comprising the polymers described herein, and the organocatalysts described herein. In some variations that may be combined with the foregoing aspects, the organocatalyst is a nitrogen-containing carbene compound. In certain variations, the organocatalyst is an N-heterocyclic carbene.

DETAILED DESCRIPTION

The following description sets forth exemplary methods, parameters and the like. It should be recognized, however, that such description is not intended as a limitation on the scope of the present disclosure but is instead provided as a description of exemplary embodiments.

Provided herein are furan or tetrahydrofuran polymer compositions that have a low metal content. Such compositions are made up of furan or tetrahydrofuran carboxylate polymers. Examples of such polymers include poly(alkylene-2,5-furandicarboxylate) or poly(alkylene-2,5-tetrahydrofurandicarboxylate). In one variation, the polymer is poly(ethylene-2,5-furandicarboxylate), and may also be referred to as "PEF". In another variation, the polymer is poly(ethylene-2,5-tetrahydrofurandicarboxylate).

In some variations, the polymer compositions herein have a low metal content. Such metal content may include the content of transition metals, post-transition metals, metalloids, and/or lanthanoid metals. In some variations, the metal content excludes the content of alkali metals, alkaline earth metals, and silicon.

In other variations, the polymer compositions herein are free from metal catalysts or residues thereof. Such metal catalysts may include, for example, transesterification catalysts. In one variation, residues of metal catalyst may include metal components or metal parts from the catalysts used in the synthesis of the polymer.

In yet other variations, the polymer compositions herein have a metal content that does not come from metal catalysts used to produce the polymer or precursors thereof. It should be understood that the trace amount of metals described herein may come from starting materials without metal catalysts. As described herein, the metal content may include the content of transition metals, post-transition metals, metalloids, and/or lanthanoid metals.

The polymer compositions herein may be produced without the use of metal catalysts. For example, such low metal content in the polymer composition may be achieved by the use of organocatalysts to produce the polymer compositions. In some variation, the polymer compositions herein comprise a residue from the organocatalyst. In some variation, the polymer compositions herein comprise a nitrogen content that comes from organocatalysts used in the polymerization. In some embodiments, the amount of nitrogen content corresponds to the amount of organocatalysts used. It should be understood that the polymer composition prepared with the use of organocatalysts may contain residue of the organocatalyst. In some embodiments, the organocatalyst is an N-heterocyclic carbene (NHC carbene).

In some variation, the polymer compositions herein are free of a residue from the enzymes and/or acid chlorides. In some variation, the polymer compositions herein comprise a nitrogen content that does not comes from enzymes and acid chlorides. In some embodiments, the organocatalyst excludes enzymes and acid chlorides.

The polymer compositions and the methods to produce such polymer compositions are described in further detail below.

Methods of Producing Polymer Compositions

Provided are methods of producing the polymer compositions described herein.

In some aspects, a furan or tetrahydrofuran compound is transesterified to produce the polymer compositions as described herein. In certain embodiments, the furan or tetrahydrofuran compound is transesterified in the presence of an organocatalyst. For example, in some variations, the furan or tetrahydrofuran compound is a compound of formula (G):

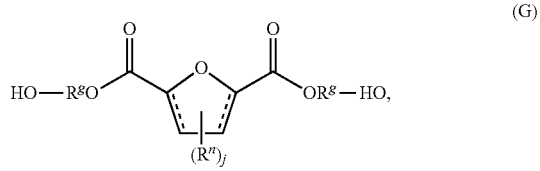

wherein:
 === is a double bond or a single bond;
 j is 2 when === is a double bond, or j is 6 when === is a single bond j;
 each $R''$ is independently H, aliphatic or aromatic; and
 each $R^g$'s independently aliphatic or aromatic, wherein the $R^g$ is optionally substituted with one or more hydroxyl groups.

General scheme 1 below depicts an exemplary reaction to produce a furan or tetrahydrofuran polymer from a compound of formula (G) using an organocatalyst.

General scheme 1

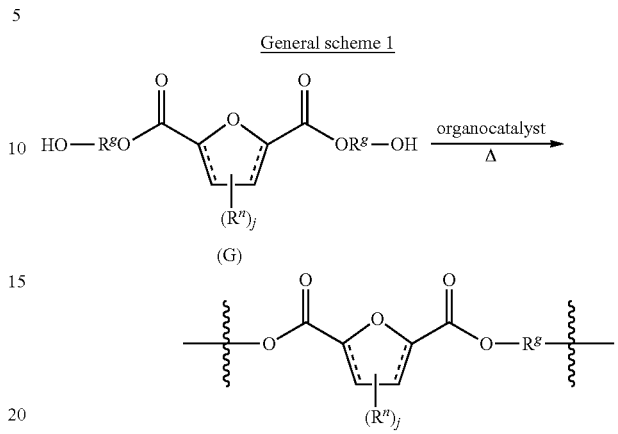

The compound of formula (G) and the organocatalysts suitable for use in the methods herein is described in further detail below. The methods described herein may be performed at any suitable temperature, for example from 200° C. to 250° C. In some variations, the methods described herein may be performed at reduced pressure. For example, in some variations the methods are performed below 100 torr, below 10 torr, or below 0.1 torr. As used herein, torr is on an absolute scale.

In other embodiments, the furan or the tetrahydrofuran is transesterified in the presence of an organocatalyst to produce a prepolymer composition; and the prepolymer is polycondensed to produce the polymer composition. In other embodiments, the furan or the tetrahydrofuran is transesterified in the presence of an organocatalyst to produce a prepolymer composition; and the prepolymer is polycondensed to produce the polymer composition. In some embodiments, the furan or the tetrahydrofuran is a compound of formula (G) as described herein.

In some embodiments of the foregoing methods, the polymer is produced at a yield of at least 60%, at least 70%, at least 80%, at least 90% or at least 95%.

In other aspects, provided herein are methods of producing a polymer or mixture of polymers from furans and diols in the presence of an organocatalyst.

In one embodiment, a furan and a diol are combined in the presence of an organocatalyst, and the furan is esterified by at least a portion of the diol to produce the polymer composition. In some embodiments, the furan is a furandicarboxylic acid, and the furandicarboxylic acid is esterified by the diol to produce the polymer composition. For example, in one variation, the furandicarboxylic acid is 2,5-furandicarboxylic acid. In other embodiments, the furan is a furandicarboxylic acid diester, and the furandicarboxylic acid diester is esterified by the diol, wherein the esterification is transesterification, to produce the polymer composition. For example, in one variation, the furandicarboxylic acid diester is 2,5-furandicarboxylic acid diester.

In another embodiment, the furan is combined with a diol in the presence of an organocatalyst. In such an embodiment, at least a portion of the furan is esterified with at least a portion of the diol to produce a prepolymer composition; and the prepolymer is polycondensed to produce the polymer composition. In certain variations, the furan is a furandicarboxylic acid diester, and the furandicarboxylic acid diester is esterified by the diol to produce the prepolymer composition, wherein the esterification is transesterification. For example, in one variation, the furandicarboxylic acid diester is 2,5-furandicarboxylic acid diester. In other variations, the polycondensation occurs in the presence of a catalyst. In certain embodiments, the catalyst for polycondensation is the same as the catalyst for the esterification, and for example, may be an organocatalyst. In other variations, the catalyst for polycondensation is different from the catalyst for esterification, and any suitable catalysts known in the art for the polycondensation step may be employed.

In another embodiment, the furan is combined with a diol in the presence of an organocatalyst. In such an embodiment, at least a portion of the furan is esterified with at least a portion of the diol to produce a prepolymer composition; the prepolymer is polycondensed to produce a polymer condensate composition; and the polymer condensate composition is dried and/or crystallized to produce the polymer composition. In certain variations, the furan is a furandicarboxylic acid diester, and the furandicarboxylic acid diester is esterified by the diol to produce the prepolymer composition, wherein the esterification is transesterification. For example, in one variation, the furandicarboxylic acid diester is 2,5-furandicarboxylic acid diester. In other variations, the polycondensation occurs in the presence of a catalyst. In certain embodiments, the catalyst for polycondensation is the same as the catalyst for the esterification, and for example, may be an organocatalyst. In other variations, the catalyst for polycondensation is different from the catalyst for esterification, and any suitable catalysts known in the art for the polycondensation step may be employed. In some embodiments, the polycondensation is transesterification.

The embodiments described above may also be performed using a tetrahydrofuran. For example, in other aspects, provided herein are methods of producing a polymer or mixture of polymers from tetrahydrofurans and diols in the presence of an organocatalyst.

In some variations, a tetrahydrofuran and a diol are combined in the presence of an organocatalyst, and the tetrahydrofuran is esterified by at least a portion of the diol to produce the polymer composition.

In other variations, the tetrahydrofuran is combined with a diol in the presence of an organocatalyst. In such a variation, at least a portion of the tetrahydrofuran is esterified with at least a portion of the diol to produce a prepolymer composition; and the prepolymer is polycondensed to produce the polymer composition.

In yet other variations, the tetrahydrofuran is combined with a diol in the presence of an organocatalyst. In such a variation, at least a portion of the tetrahydrofuran is esterified with at least a portion of the diol to produce a prepolymer composition; the prepolymer is polycondensed to produce a polymer condensate composition; and the polymer condensate composition is dried and/or crystallized to produce the polymer composition.

The polymerization described above may be carried out below 300° C. In some embodiments, the polymerization is carried out at 250° C., at 230° C., at 200° C., at 180° C., at 170° C., at 160° C., or at 150° C. During polymerization, the polymer or prepolymer composition may be heated for at least 3 hours, at least 5 hours, at least 10 hours, at least 15 hours, at least 20 hours, at least 48 hours, at least 60 hours, or more. In other embodiments, the polymer or prepolymer composition is heated for between 3 to 5 hours, between 5 to 10 hours, between 10 to 15 hours, between 15 to 24 hours, between 24 to 48 hours, or between 48 to 60 hours.

Reduced Color Content

As described above, the polymer compositions described herein may be produced by polymerizing a furan or tetrahydrofuran in the presence of an organocatalyst; polymerizing a furan and a diol in the presence of an organocatalyst; or producing a prepolymer composition from a furan and then further polymerizing the prepolymer composition. In some embodiments, the methods described herein may reduce the color content of the polymer composition. For example, the use of antioxidant compounds, or performing the polymerization at reduced temperature, or a combination thereof, may reduce the color content of the polymer composition.

In certain embodiments, a polymer composition with reduced color is produced by carrying out polymerization in the presence of one or more antioxidant compounds. In certain embodiments, a polymer composition with reduced color is produced by carrying out polymerization in the presence of one or more antioxidant compounds and at reduced temperature.

In certain variations, the antioxidant compound may comprise a phosphite, a bisphosphite, a phosphate, or a polymer antioxidant, or any combinations thereof. To give an example, tris(2,4-di-tert-butylphenyl) phosphite can be used. Suitable commercially available phosphites can be used. In some variations, the phosphite is Weston® TNPP phosphite. In some variations, the phosphite is Weston® 705 phosphite. In other variations, the polymer antioxidant is Irganox® 1010 or Irgafos® 126. In other variations, the phosphate antioxidant compound comprises an optionally mono-, di-, or tri-substituted phosphate, wherein the substituents are independently alkyl or aryl. Mixtures of any of these antioxidant compounds may also be used. The antioxidant compound used may be a solid, a liquid, or a combination thereof.

In some embodiments, the polymer composition having reduced color content may be produced by carrying out the polymerization at reduced temperature. In certain embodiments, the reduced temperature is the temperature between the range of the glass transition temperature ($T_g$) and the melting temperature ($T_m$) of the polymer. In some embodiments, the polymerization is carried out below 200° C. to produce a polymer composition having reduced color content. In other embodiments, the reduced temperature is between the range of the $T_g$ and $T_m$ of the polymer and is lower than 200° C.

In certain embodiments, a polymer composition with reduced color is produced by carrying out polymerization in the presence of one or more antioxidant compounds and at reduced temperature.

In other variations, a polymer composition with reduced color content is produced by carrying out polymerization in the presence of one or more antioxidant compounds to produce an initial polymer or prepolymer composition, then subjecting the initial polymer or prepolymer composition to solid state polymerization to produce the polymer composition with reduced color content.

In some embodiments, the polymerization as described above is carried out in the presence of one or more stabilizing agents. In some embodiments, the stabilizing agent is phosphoric acid. In certain embodiments, the stabilizing agent is not an antioxidant.

In still other embodiments, the color content of the polymer composition may be reduced by performing the polymerization in solution phase under reduced pressure. In certain embodiments, the polymerization may be performed under solution phase in a high boiling solvent under reduced pressure to produce a polymer composition with reduced color content. Such solvent may comprise, for example, sulfolane, dimethyl sulfoxide (DMSO), or combinations thereof. In some embodiments, the polymer composition produced may then undergo solid state polymerization.

Solid State Polymerization

In some variations, solid state polymerization may be used to produce a polymer composition with a higher molecular weight (e.g., $M_n$ and/or $M_w$). For example, the polymer or prepolymer compositions described herein may undergo solid state polymerization (SSP) to produce a polymer composition with a higher molecular weight. In some embodiments, SSP is used to produce a polymer composition with reduced color content.

Solid state polymerization (SSP) may include heating a polymer, or prepolymer composition, above the $T_g$ but below the $T_m$ of the polymer or prepolymer composition. The polymer or prepolymer composition may be produced according to any of the polymerization methods described herein. In some variations, annealing is carried out before the polymer, or prepolymer composition undergos SSP. In some embodiments, the annealing temperature is at 140° C. During annealing, the polymer or prepolymer composition may be heated for at least 3 hours, at least 5 hours, at least 10 hours, at least 15 hours, at least 20 hours, at least 48 hours, at least 60 hours, or more. In other embodiments, the polymer or prepolymer composition is heated for between 5 to 10 hours, between 10 to 15 hours, between 15 to 24 hours, between 24 to 48 hours, between 48 to 60 hours, between 60 to 80 hours, between 80 to 110 hours, between 110 to 150 hours, or between 48 to 150 hours.

Then, this polymer or prepolymer composition may undergo SSP to produce an SSP polymer composition. SSP may include heating the polymer or prepolymer composition to a temperature lower than the polymerization temperature used to produce the polymer or prepolymer composition. In some embodiments, temperature of SSP is between the glass transition temperature ($T_g$) and the melting temperature ($T_m$) of the polymer or prepolymer composition. In certain embodiments, the SSP temperature is maintained at 10° C. below $T_m$. In other embodiments, the SSP temperature is maintained at 30° C. below $T_m$. In certain embodiments, the SSP temperature is at 180° C.

During SSP, the polymer or prepolymer composition may be heated for at least 5 hours, at least 10 hours, at least 15 hours, at least 24 hours, at least 48 hours, at least 60 hours, at least 70 hours, at least 100 hours, at least 130 hours, or more. In other embodiments, the polymer or prepolymer composition is heated for between 5 to 10 hours, between 10 to 15 hours, between 15 to 24 hours, between 24 to 48 hours, between 48 to 60 hours, between 60 to 80 hours, between 80 to 110 hours, between 110 to 150 hours, or between 48 to 150 hours. In some embodiments, the polymer or prepolymer composition is heated to between the $T_g$ but below the $T_m$ until the desired $M_n$ is reached, which may be determined, for example, by monitoring the $M_n$, $M_w$, or both of the heated composition by analyzing samples with GPC or with $H^1$-NMR.

In some embodiments, SSP is carried out under an inert atmosphere (e.g., nitrogen or helium), or under reduced pressure (e.g., less than 100 torr). After period of time being heated between the $T_g$ and the $T_m$, the resulting SSP polymer composition is cooled, for example to room temperature. Carrying out SSP with a polymer composition or prepolymer composition may produce an SSP polymer composition that has a higher $M_n$, higher $M_w$ or both, compared to the polymer or polymer composition that has not undergone SSP. This may be determined, for example, by GPC analysis using polystyrene standards.

In some embodiments, the polymer composition or prepolymer composition which is going to undergo SSP has a low water content, such as less than 1% wt, less than 0.5 wt %, less than 0.1 wt %, less than 0.05 wt %, less than 0.01 wt % water, or less than 0.005 wt % water. In some embodiments, the composition during SSP has a low water content, such as less than 1% wt, less than 0.5 wt %, less than 0.1 wt %, less than 0.05 wt %, less than 0.01 wt % water, or less than 0.005 wt % water. In other embodiments, the polymer composition or prepolymer composition comprises water.

In some embodiments, the polymer or prepolymer composition prior to SSP has an $M_n$ of less than 5,000 Da, less than 10,000 Da, less than 12,000 Da, less than 15,000 Da, less than 18,000 Da, or less than 20,000 Da. In some embodiments, the $M_n$ of the SSP polymer composition (after the polymer or prepolymer composition has undergone SSP) is greater than 20,000 Da, greater than 25,000 Da, greater than 30,000 Da, greater than 35,000 Da, greater than 40,000 Da, greater than 45,000 Da, or greater than 50,000 Da.

In some embodiments, the polymer or prepolymer composition prior to SSP has an $M_w$ of less than 5,000 Da, less than 10,000 Da, less than 12,000 Da, less than 15,000 Da, less than 18,000 Da, less than 20,000 Da, less than 25,000 Da, less than 30,000 Da, less than 35,000 Da, and less than 40,000 Da. In some embodiments, the $M_w$ of the SSP polymer composition (after the polymer or prepolymer composition has undergone SSP) is greater than 10,000 Da, greater than 14,000 Da, greater than 18,000 Da, greater than 20,000 Da, greater than 25,000 Da, greater than 30,000 Da, greater than 35,000 Da, greater than 40,000 Da, greater than 45,000 Da, greater than 50,000 Da, greater than 55,000 Da, or greater than 60,000 Da.

As described above, in some embodiments polymerization in the presence of one or more antioxidant compounds is combined with SSP. In certain embodiments, SSP may be performed in the presence of one or more antioxidant compounds, including any of the antioxidant compounds or combinations thereof described above.

Reaction Mixture

In some embodiments, a compound of formula (G) is combined with an organocatalyst to form a reaction mixture. The compound of formula (G) may be a furan or a tetrahydrofuran compound. For example, in certain embodiments, the furan is combined with the diol to form a reaction mixture. In certain embodiments, the furan is combined with the diol and an organocatalyst to form a reaction mixture. In certain variations, the tetrahydrofuran is combined with the diol to form a reaction mixture. In certain embodiments, the tetrahydrofuran is combined with the diol and an organocatalyst to form a reaction mixture.

In some variations, the reaction mixture has less than 1 wt % metal, less than 0.5 wt % metal, less than 0.3 wt % metal, less than 0.1 wt % metal, less than 0.05 wt % metal, less than 0.04 wt % metal, less than 0.03 wt % metal, less than 0.02 wt % metal, less than 0.01 wt % metal, less than 0.009 wt % metal, less than 0.006 wt % metal, less than 0.003 wt % metal, less than 0.001 wt % metal, less than 0.0009 wt % metal, less than 0.0006 wt % metal, less than 0.0003 wt % metal, less than 0.0001 wt % metal, or less than 0.00009 wt % metal. In some variations, the reaction mixture has less than 0.09 wt % metal, less than 0.08 wt % metal, less than 0.07 wt % metal, less than 0.06 wt % metal, less than 0.05 wt % metal, less than 0.04 wt % metal, less than 0.03 wt % metal, or less than 0.02 wt % metal.

As used herein, "wt %" of element M in a composition refers to (mass of element M/dry mass of composition)× 100%. One skilled in the art would also appreciate how to convert wt % to ppm.

In some variations, the metal is one or more transition metals, one or more post-transition metals, one or more metalloids, one or more lanthanoid metals, or any combination thereof.

In certain embodiments, the total transition metal content of the reaction mixture is less than 1 wt %, less than 0.5 wt %, less than 0.3 wt %, less than 0.1 wt %, less than 0.05 wt %, less than 0.04 wt %, less than 0.03 wt %, less than 0.02 wt %, less than 0.01 wt %, less than 0.009 wt %, less than 0.006 wt %, less than 0.003 wt %, less than 0.001 wt %, less than 0.0009 wt %, less than 0.0006 wt %, less than 0.0003 wt %, less than 0.0001 wt %, or less than 0.00009 wt %.

In some variations, the compound of formula (G) is combined with an organocatalyst to form a reaction mixture. In certain embodiments, the furan is combined with the diol to form a reaction mixture. In certain embodiments, the furan is combined with the diol and an organocatalyst to form a reaction mixture. In other embodiments, the tetrahydrofuran is combined with the diol to form a reaction mixture. In certain embodiments, the tetrahydrofuran is combined with the diol and an organocatalyst to form a reaction mixture.

In some variations, the reaction mixture has less than 1 mol % metal, less than 0.5 mol % metal, less than 0.3 mol % metal, less than 0.1 mol % metal, less than 0.05 mol % metal, less than 0.04 mol % metal, less than 0.03 mol % metal, less than 0.02 mol % metal, less than 0.01 mol % metal, less than 0.009 mol % metal, less than 0.006 mol % metal, less than 0.003 mol % metal, less than 0.001 mol % metal, less than 0.0009 mol % metal, less than 0.0006 mol % metal, less than 0.0003 mol % metal, less than 0.0001 mol % metal, or less than 0.00009 mol % metal relative to the compound of formula (G), which may include the furan or the tetrahydrofuran.

In some variations, the metal is one or more transition metals. The transition metal may include an element of the d-block of the periodic table, including groups 3 to 12. In certain embodiments, the transition metal is scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, rutherfordium, dubnium, seaborgium, bohrium, hassium, meitnerium, darmstadtium, roentgenium, or copernicium.

In other variations, the metal is one or more lanthanoids. The lanthanoid may include an element with an atomic number from 57 to 71. In certain embodiments, the lanthanoid is lanthanum, cerium, praseodymium, neodymium, promethium, samarium, europium, gadolinium, terbium, dysprosium, holmium, erbium, thulium, ytterbium, or lutetium.

In some variations, the metal is a post-transition metal. In some embodiments, the post-transition metal is gallium, indium, thallium, tin, lead, bismuth, or aluminum.

In still other variations, the metal is a metalloid. In some embodiments, the metalloid is boron, silicon, germanium, arsenic, antimony, tellurium, or polonium.

In one variation, the metal excludes alkali metals, alkaline earth metals, and silicon.

In certain embodiments, the transition metal content, the lanthanoid metal content, the post-transition metal content, the metalloid content, or any combination thereof of the reaction mixture is less than 1 mol %, less than 0.5 mol %, less than 0.3 mol %, less than 0.1 mol %, less than 0.05 mol %, less than 0.04 mol %, less than 0.03 mol %, less than 0.02 mol %, less than 0.01 mol %, less than 0.009 mol %, less than 0.006 mol %, less than 0.003 mol %, less than 0.001 mol %, less than 0.0009 mol %, less than 0.0006 mol %, less than 0.0003 mol %, less than 0.0001 mol %, or less than 0.00009 mol % relative to the compound of formula (G), which may include the furan or the tetrahydrofuran.

In some variations, the reaction mixture comprises less than 400 ppm, less than 350 ppm, less than 300 ppm, less than 250 ppm, less than 200 ppm, less than 150 ppm, less than 100 ppm, less than 50 ppm, less than 25 ppm, less than 10 ppm, less than 8 ppm, less than 6 ppm, less than 5 ppm, less than 3 ppm, less than 1 wt %, less than 0.5 wt %, less than 0.3 wt %, less than 0.1 wt %, less than 0.05 wt %, less than 0.04 wt %, less than 0.03 wt %, less than 0.02 wt %, less than 0.01 wt %, less than 0.009 wt %, less than 0.006 wt %, less than 0.003 wt %, less than 0.001 wt %, less than 0.0009 wt %, less than 0.0006 wt %, less than 0.0003 wt %, less than 0.0001 wt %, or less than 0.00009 wt % of one or more of scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, rutherfordium, dubnium, seaborgium, bohrium, hassium, meitnerium, darmstadtium, roentgenium, copernicium, lanthanum, cerium, praseodymium, neodymium, promethium, samarium, europium, gadolinium, terbium, dysprosium, holmium, erbium, thulium, ytterbium, lutetium, gallium, indium, thallium, tin, lead, bismuth, boron, silicon, germanium, arsenic, antimony, or tellurium.

In some variations, the total content of scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, rutherfordium, dubnium, seaborgium, bohrium, hassium, meitnerium, darmstadtium, roentgenium, and copernicium in the reaction mixture (if present) is less than 400 ppm, less than 350 ppm, less than 300 ppm, less than 250 ppm, less than 200 ppm, less than 150 ppm, less than 100 ppm, less than 50 ppm, less than 25 ppm, less than 10 ppm, less than 1 wt %, less than 0.5 wt %, less than 0.3 wt %, less than 0.1 wt %, less than 0.05 wt %, less than 0.04 wt %, less than 0.03 wt %, less than 0.02 wt %, less than 0.01 wt %, less than 0.009 wt %, less than 0.006 wt %, less than 0.003 wt %, less than 0.001 wt %, less than 0.0009 wt %, less than 0.0006 wt %, less than 0.0003 wt %, less than 0.0001 wt %, or less than 0.00009 wt %.

In some embodiments, the total content of lanthanum, cerium, praseodymium, neodymium, promethium, samarium, europium, gadolinium, terbium, dysprosium, holmium, erbium, thulium, ytterbium, and lutetium in the reaction mixture (if present) is less than 400 ppm, less than 350 ppm, less than 300 ppm, less than 250 ppm, less than 200 ppm, less than 150 ppm, less than 100 ppm, less than 50 ppm, less than 25 ppm, less than 10 ppm, less than 1 wt %, less than 0.5 wt %, less than 0.3 wt %, less than 0.1 wt %, less than 0.05 wt %, less than 0.04 wt %, less than 0.03 wt %, less than 0.02 wt %, less than 0.01 wt %, less than 0.009 wt %, less than 0.006 wt %, less than 0.003 wt %, less than 0.001 wt %, less than 0.0009 wt %, less than 0.0006 wt %, less than 0.0003 wt %, less than 0.0001 wt %, or less than 0.00009 wt %.

In some embodiments, the total content of gallium, indium, thallium, tin, lead, and bismuth in the reaction mixture (if present) is less than 400 ppm, less than 350 ppm, less than 300 ppm, less than 250 ppm, less than 200 ppm, less than 150 ppm, less than 100 ppm, less than 50 ppm, less than 25 ppm, less than 10 ppm, less than 1 wt %, less than 0.5 wt %, less than 0.3 wt %, less than 0.1 wt %, less than 0.05 wt %, less than 0.04 wt %, less than 0.03 wt %, less than 0.02 wt %, less than 0.01 wt %, less than 0.009 wt %, less than 0.006 wt %, less than 0.003 wt %, less than 0.001 wt %, less than 0.0009 wt %, less than 0.0006 wt %, less than 0.0003 wt %, less than 0.0001 wt %, or less than 0.00009 wt %.

In some embodiments, the total content of boron, silicon, germanium, arsenic, antimony, and tellurium in the reaction mixture (if present) is less than 400 ppm, less than 350 ppm, less than 300 ppm, less than 250 ppm, less than 200 ppm, less than 150 ppm, less than 100 ppm, less than 50 ppm, less than 25 ppm, less than 10 ppm, less than 1 wt %, less than 0.5 wt %, less than 0.3 wt %, less than 0.1 wt %, less than 0.05 wt %, less than 0.04 wt %, less than 0.03 wt %, less than 0.02 wt %, less than 0.01 wt %, less than 0.009 wt %, less than 0.006 wt %, less than 0.003 wt %, less than 0.001 wt %, less than 0.0009 wt %, less than 0.0006 wt %, less than 0.0003 wt %, less than 0.0001 wt %, or less than 0.00009 wt %.

In some embodiments, the total content of aluminium, titanium, vanadium, chromium, manganese, iron, cobalt, zinc, geranium, zirconium, cadmium, tin, antimony, hafnium, tungsten, lead, and bismuth in the reaction mixture (if present) is less than 400 ppm, less than 350 ppm, less than 300 ppm, less than 250 ppm, less than 200 ppm, less than 150 ppm, less than 100 ppm, less than 50 ppm, less than 25 ppm, less than 10 ppm, less than 1 wt %, less than 0.5 wt %, less than 0.3 wt %, less than 0.1 wt %, less than 0.05 wt %, less than 0.04 wt %, less than 0.03 wt %, less than 0.02 wt %, less than 0.01 wt %, less than 0.009 wt %, less than 0.006 wt %, less than 0.003 wt %, less than 0.001 wt %, less than 0.0009 wt %, less than 0.0006 wt %, less than 0.0003 wt %, less than 0.0001 wt %, or less than 0.00009 wt %.

In certain variations, the reaction mixture comprises less than 400 ppm, less than 300 ppm, less than 200 ppm, less than 100 ppm, less than 50 ppm, less than 25 ppm, or less than 10 ppm of tin. In certain embodiments, the combination of transition metals and tin in the reaction mixture is less than 400 ppm, less than 300 ppm, less than 200 ppm, less than 100 ppm, or less than 50 ppm.

In some variations, the reaction mixture has a total transition metal content of less than 0.016 wt %, a total lanthanoid content of less than 0.01 wt %, a total post-transition metal content of less than 0.0075 wt %, and a total metalloid content of less than 0.02 wt %.

It should be understood that the metal contents described herein may be combined as if each and every combination were individually listed. For example, in one variation, the reaction mixture has less than 0.000738 wt % of scandium, less than 0.000635 wt % of titanium, less than 0.000456 wt % of vanadium, less than 0.000265 wt % of chromium, less than 0.000145 wt % of manganese, less than 0.00130 wt % of iron, less than 0.000089 wt % of cobalt, less than 0.000380 wt % of nickel, less than 0.000104 wt % of copper, less than 0.00040 wt % of zinc, less than 0.000379 wt % of yttrium, less than 0.000442 wt % of zirconium, less than 0.000505 wt % of niobium, less than 0.000710 wt % of molybdenum, less than 0.000875 wt % of technetium, less than 0.000869 wt % of ruthenium, less than 0.001359 wt % of rhodium, less than 0.001391 wt % of palladium, less than 0.001273 wt % of silver, less than 0.001497 wt % of cadmium, less than 0.000197 wt % of hafnium, less than 0.000197 wt % of tantalum, less than 0.000223 wt % of tungsten, less than 0.000297 wt % of rhenium, less than 0.000190 wt % of osmium, less than 0.000212 wt % of iridium, less than 0.000249 wt % of platinum, less than 0.000243 wt % of gold, or less than 0.000282 wt % of mercury, or any combinations thereof.

In another variation, the reaction mixture has less than 0.001998 wt % of lanthanum, less than 0.001440 wt % of cerium, less than 0.001161 wt % of praseodymium, less than 0.000929 wt % of neodymium, less than 0.00077 wt % of promethium, less than 0.00053 wt % of samarium, less than 0.00041 wt % of europium, less than 0.00038 wt % of gadolinium, less than 0.00037 wt % of terbium, less than 0.00042 wt % of dysprosium, less than 0.00025 wt % of holmium, less than 0.00025 wt % of erbium, less than 0.00022 wt % of thulium, less than 0.00027 wt % of ytterbium, or less than 0.00018 wt % of lutetium, or any combinations thereof.

In yet another variation, the reaction mixture has less than 0.000078 wt % of gallium, less than 0.004280 wt % of indium, less than 0.002394 wt % of tin, less than 0.000299 wt % of lead, or less than 0.000330 wt % of bismuth, or any combinations thereof.

In yet another variation, the reaction mixture has less than 0.01478 wt % of silicon, less than 0.000089 wt % of germanium, less than 0.00010 wt % of arsenic, less than 0.002701 wt % of antimony, or less than 0.002032 wt % of tellurium, or any combinations thereof.

In yet another variation, the reaction mixture has less than 0.0026 wt % of aluminium, 0.00064 wt % of titanium, 0.00046 wt % of vanadium, 0.00027 wt % of chromium, 0.00015 wt % of manganese, 0.0014 wt % of iron, 0.00009 wt % of cobalt, 0.0004 wt % of zinc, 0.00009 wt % of geranium, 0.0004 wt % of zirconium, 0.0015 wt % of cadmium, 0.0024 wt % of tin, 0.0027 wt % of antimony, 0.00019 wt % of hafnium, 0.00022 wt % of tungsten, 0.00029 wt % of lead, or 0.00033 wt % of bismuth, or any combinations thereof.

It should further be understood that a reaction mixture with a certain level of metal content (which may include the content of transition metal, lanthanoid, post-transition metal, or metalloid, or any combinations thereof) may have other levels of non-transition metals, non-lanthanoids, non-post-transition metals, or non-metalloids, or combinations thereof. For example, in some embodiments, the total content of transition metals in the reaction mixture is less than 150 ppm, while the total content of alkali metals, alkaline earth metals, or a combination thereof is greater than 50 ppm, greater than 100 ppm, greater than 200 ppm, greater than 300 ppm, or greater than 400 ppm. In some variations, the total content of transition metals in the reaction mixture is less than 150 ppm, while the total content of sodium, magnesium, or a combination thereof is greater than 50 ppm, greater than 75 ppm, greater than 100 ppm, greater than 150 ppm, or greater than 200 ppm.

In some variations of the foregoing embodiments, the metal is a transition metal, or a heavy metal, or a combination thereof. In other variations, the metal is tin, zirconium, hafnium, antimony, or germanium, or any combinations thereof. In certain variations, the tin may be tin(IV) or tin(II), or a combination thereof. In other variations, the metal is lead, titanium, bismuth, zinc, cadmium, aluminum, manganese, cobalt, chromium, iron, tungsten, or vanadium, or any combinations thereof. In certain variations, the metal is tin, zirconium, hafnium, antimony, germanium, titanium, zinc, or aluminum, or any combinations thereof. One or more metals may contribute to the metal content present in the reaction mixture.

In some variations the reaction mixture has a metal content of less 0.025 wt %, wherein the metal content is based on Group II metals, transition metals, post-transition metals, metalloids, and/or lanthanoids (if present), provided that the metal content does not include the content of titanium or tin (if present).

In some variations the reaction mixture has a metal content of less 0.02 wt %, wherein the metal content is based on Group II metals, transition metals, post-transition metals, metalloids, and/or lanthanoids (if present), provided that the metal content does not include the content of tin (if present).

In some variations the reaction mixture has a metal content of less 0.003 wt %, wherein the metal content is based on transition metals, post-transition metals, metalloids, and/or lanthanoids (if present).

The furans, diols (if used), catalyst and reaction conditions to produce polymer compositions are described in further detail below.

Furans and Tetrahydrofurans

The polymer compositions described herein, which may include a polymer or a mixture of polymers, may be produced by combining at least one optionally substituted furan or tetrahydrofuran with at least one diol in the presence of an organocatalyst. In some variations of the foregoing, the furan or tetrahydrofuran may be substituted with one or more aliphatic or aromatic groups.

In some variations, the furan or tetrahydrofuran is a compound of formula (F):

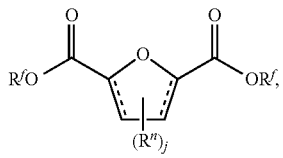

(F)

wherein:
  === is a double bond or a single bond;
  j is 2 when === is a double bond, or j is 6 when === is a single bond j;
  each $R''$ is independently H, aliphatic, or aromatic; and
  each $R^f$ is independently H, aliphatic, or aromatic.

In one embodiment, the aliphatic is alkyl. In some embodiments, each $R''$ is independently H or alkyl. In some variations, === is a double bond, j is 2, and the compound of formula (F) is a compound of formula (F1):

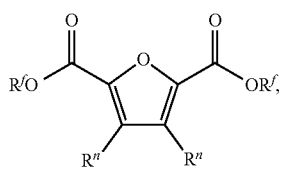

(F1)

wherein each $R''$ is independently H, aliphatic or aromatic, and each $R^f$ is independently H, aliphiatic or aromatic. In some variations each $R''$ is independently H or alkyl. In some variations, each $R^f$ is independently H or alkyl.

In some variations, each $R''$ is H. In other variations, one $R''$ is alkyl and the other $R''$ is H. In yet other variations, both $R''$ are alkyl. In some variations, each $R''$ is independently selected from H, methyl, ethyl, propyl, butyl, and pentyl. In some variations, each $R^f$ is H. In other variations, one $R^f$ is alkyl and the other $R^f$ is H. In yet other variations, both $R^f$ are alkyl. In some variations, each $R^f$ is independently selected from H, methyl, ethyl, propyl, butyl, and pentyl.

In some variations, each $R''$ and $R^f$ is H, and the compound of formula (F1) is 2,5-furandicarboxylic acid (FDCA):

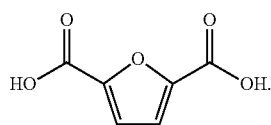 [SMILES: O=C(O)c1ccc(C(=O)O)o1]

In some variations, each $R''$ is H, each $R^f$ is methyl, and the compound of formula (F1) is 2,5-furandicarboxylic acid (FDCA) dimethyl ester:

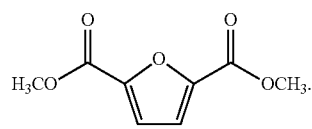 [SMILES: COC(=O)c1ccc(C(=O)OC)o1]

In yet other variations, each $R''$ is H, each $R^f$ is ethyl, and the compound of formula (F1) is 2,5-furandicarboxylic acid (FDCA) diethyl ester:

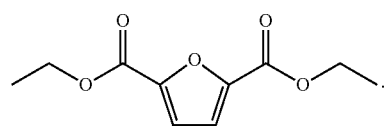

In other variations of the methods described herein, === is a single bond, j is 6, and the compound of formula (F) is a compound of formula (F2):

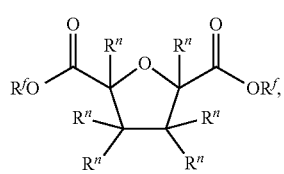

(F2)

wherein each $R''$ and each $R^f$ are independently H, aliphatic or aromatic. In some variations, each $R''$ is independently H or alkyl. In some variations, each $R^f$ is independently H or alkyl.

In some variations, each $R''$ is H. In certain variations, one $R''$ is alkyl and each of the remaining $R''$ is H. In other variations, two $R''$ are independently alkyl, and each of the remaining $R''$ is H. In other variations, three $R''$ are independently alkyl, and each of the remaining $R''$ is H. In still other variations, four $R''$ are independently alkyl, and each of the remaining R″ is H. In yet other variations, five R″ are independently alkyl, and the remaining R″ is H. In other variations, each R″ is independently alkyl. In some variations, each R″ is independently selected from H, methyl, ethyl, propyl, butyl, and pentyl. In some variations, each R^f is H. In other variations, one R^f is alkyl and the other R^f is H. In yet other variations, both R^f are alkyl. In some variations, each R^f is independently selected from H, methyl, ethyl, propyl, butyl, and pentyl.

In certain variations, each R″ and each R^f is H, and the compound of formula (F2) is 2,5-tetrahydrofurandicarboxylic acid:

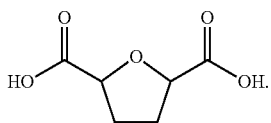 [SMILES: O=C(O)C1CCC(C(=O)O)O1]

In certain variations, each R″ is H, each R^f is methyl, and the compound of formula (F2) is 2,5-tetrahydrofurandicarboxylic acid dimethyl ester:

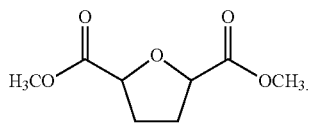 [SMILES: COC(=O)C1CCC(C(=O)OC)O1]

It should generally be understood that variables R″ and R^f for formulae (F), (F1) and (F2) may be combined as if each and every combination were individually listed.

Compounds of Formula (G)

The polymer compositions described herein, which may include a polymer or a mixture of polymers, may also be produced by combining at least one optionally substituted furan or tetrahydrofuran with an organocatalyst. In some variations of the foregoing, the furan or tetrahydrofuran may be substituted with one or more aliphatic or aromatic groups. In some variations, the aliphatic is alkyl. Thus, in some variations, the furan or tetrahydrofuran may be substituted with one or more alkyl groups.

In some variations, the furan or tetrahydrofuran is a compound of formula (G):

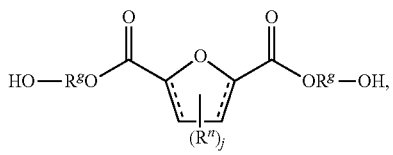

wherein:
=== is a double bond or a single bond;
j is 2 when === is a double bond, or j is 6 when === is a single bond j;
each R″ is independently H, aliphatic or aromatic; and
each R^g is independently aliphatic or aromatic, wherein the R^g is optionally substituted with one or more hydroxyl groups.

In some embodiments, the aliphatic is alkyl. In some embodiments, each R″ is independently H or alkyl. In some variations, each R^g is independently alkyl.

In some variations, === is a double bond, j is 2, and the compound of formula (G) is a compound of formula (G1):

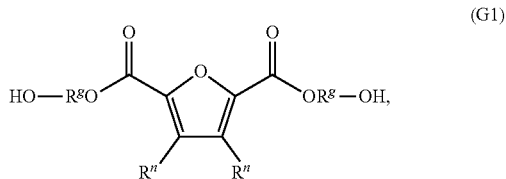

wherein:
each R″ independently H, aliphatic, or aromatic; and
each R^g is independently aliphatic or aromatic, wherein the R^g is optionally substituted with one or more hydroxyl groups.

In some variations, each R″ is independently H or alkyl. In some variations, each R^g is independently alkyl. In some variations, each R″ is H. In other variations, one R″ is alkyl and the other R″ is H. In yet other variations, both R″ are alkyl. In some variations, each R″ is independently selected from H, methyl, ethyl, propyl, butyl, and pentyl. In yet other variations, both R^g are alkyl, wherein each alkyl is independently substituted by at least one hydroxyl group. In some variations, each R^g is independently selected from the group consisting of methyl, ethyl, propyl, butyl, and pentyl.

In one variation, each R″ is H, each R^g is ethyl, and the compound of formula (G1) is bis(hydroxymethyl) furan-2,5-dicarboxylate:

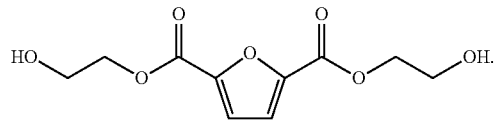 [SMILES: O=C(OCCO)c1ccc(C(=O)OCCO)o1]

In other variations of the methods described herein, === is a single bond, j is 6, and the compound of formula (G) is a compound of formula (G2):

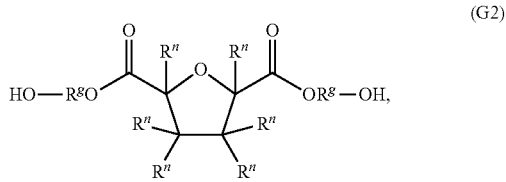

wherein:
each R″ independently H, aliphatic, or aromatic; and
each R^g is independently aliphatic or aromatic, wherein the R^g is optionally substituted with one or more hydroxyl groups.

In some variations, each R″ is independently H or alkyl. In some variations, each R″ is H. In certain variations, one R″ is alkyl and each of the remaining R″ is H. In other variations, two R″ are independently alkyl, and each of the remaining R″ is H. In other variations, three R″ are independently alkyl, and each of the remaining R″ is H. In still other variations, four R″ are independently alkyl, and each of the remaining R″ is H. In yet other variations, five R″ are independently alkyl, and the remaining R″ is H. In other variations, each R″ is independently alkyl. In some variations, each R" is independently selected from H, methyl, ethyl, propyl, butyl, and pentyl. In some variations, each $R^g$ is independently selected from the group consisting of methyl, ethyl, propyl, butyl, and pentyl.

In certain variations, each R" is H, each $R^g$ is ethyl, and the compound of formula (G2) is bis(2-hydroxyethyl) tetrahydrofuran-2,5-dicarboxylate:

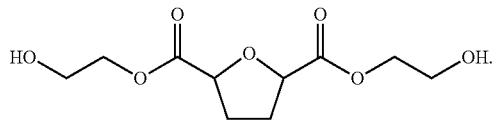 [SMILES: O=C(OCCO)C1CCC(C(=O)OCCO)O1]

It should be understood that when alkyl substituted by one or more hydroxyl groups, each hydroxyl group may be independently bonded to a primary carbon, a secondary carbon, or a tertiary carbon.

It should generally be understood that variables R" and $R^g$ for formulae (G), (G1) and (G2) may be combined as if each and every combination were individually listed.

Diol

In some variations, to produce the polymer composition described herein, at least one furan or tetrahydrofuran is combined with at least one diol in the presence of an organocatalyst, and at least a portion of the furan or the tetrahydrofuran is esterified with at least a portion of the diol.

In some variations, the diol is alkyl, alkenyl, cycloalkyl, heterocycloalkyl, aryl, heteroaryl, or ether; wherein the alkyl is substituted with two —OH groups; and wherein the alkenyl, cycloalkyl, heterocycloalkyl, aryl, heteroaryl, or ether is optionally substituted with one or more alkyl groups and is substituted with two substituents independently selected from the group consisting of —OH and —$R^P$—OH, wherein $R^P$ is alkyl. In some variations, the diol is further substituted with one or more substituents for additional functionality. The substituents may be the same or different. Any substituents that are inert to the polymerization in according with the present application can be used. Exemplary substituents include, but are not limited to, fluoro, chloro, —$OR_1$ wherein $R_1$ is alkyl, and —$C(O)NR_2R_3$, wherein $R_2$ and $R_3$ are independently H or alkyl. In certain variation, the diol is a perfluoro-diol.

In some embodiments, the diol is not substituted with any —$R^P$—OH groups. In other embodiments, the diol is substituted with at least one —OH group and at least one —$R^P$—OH group. In some embodiments, each $R^P$ is independently is methyl, ethyl, propyl, butyl, pentyl, or hexyl.

The hydroxyl groups of the diol may be independently connected to the diol at any position. For example, in some embodiments, the diol is contains two hydroxyl groups, wherein each hydroxyl group is independently bonded to a primary carbon, a secondary carbon, a tertiary carbon, or any combinations thereof.

In some variations, the diol comprises a cycloalkyl, heterocycloalkyl, aryl, heteroaryl or ether, wherein the cycloalkyl, heterocycloalkyl, aryl, heteroaryl, or ether is optionally substituted with one or more alkyl groups and is substituted with two —$R^P$—OH substituents, wherein $R^P$ is alkyl, and each —OH is independently bonded to a primary carbon, a secondary carbon, or a tertiary carbon of the $R^P$ group.

For example, in one embodiment, the diol is n-butane substituted with two hydroxyl groups each bonded to a different primary carbon. In one variation, the diol is:

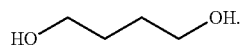

In one embodiment, the diol is ethane substituted with two hydroxyl groups each bonded to a different primary carbon. In one variation, the diol is:

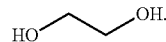

In another embodiment, the diol is cyclohexane substituted with one hydroxyl group bonded to a secondary carbon, and one —$R^P$—OH group wherein $R^P$ is methyl. In one variation, the diol is:

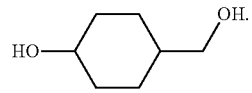

In some variations of the methods described herein, the diol is alkyl, wherein the alkyl is substituted with two hydroxyl groups. For example, in some variations, the diol is ethane-1,2-diol, 1,3-propanediol, 1,4-butanediol, 1,6-hexanediol, 1,8-octanediol, glycerol, erythritol, or pentaerythritol. In certain variations, the diol is $C_2$-$C_5$ alkyl, wherein the alkyl is substituted with two hydroxyl groups.

In some variations, the diol is alkenyl, wherein the alkenyl is optionally substituted with one or more alkyl groups and is substituted with two substituents selected from the group consisting of —OH and —$R^P$—OH, wherein $R^P$ is alkyl. In some variation, the diol is alkenyl substituted with two hydroxyl groups. In some variation, the diol is $C_2$-$C_5$ alkenyl substituted with two hydroxyl groups. In some variations, the diol is alkenyl substituted with one —OH and one —$R^P$—OH substituent. In some variations, the diol is $C_2$-$C_5$ alkenyl substituted with one —OH and one —$R^P$—OH substituent. In some variations, the diol is alkenyl substituted with two —$R^P$—OH substituents, wherein $R^P$ is independently alkyl. In some variations, the diol is $C_2$-$C_5$ alkenyl substituted with two —$R^P$—OH substituents, wherein $R^P$ is independently alkyl.

For example, in some variations, the diol is allylic diol.

In some variations, the diol is cycloalkyl, wherein the cycloalkyl is optionally substituted with one or more alkyl groups and is substituted with two substituents selected from the group consisting of —OH and —$R^P$—OH, wherein $R^P$ is alkyl. In some variation, the diol is cycloalkyl substituted with two hydroxyl groups. In some variation, the diol is $C_3$-$C_5$ cycloalkyl substituted with two hydroxyl groups. In some variations, the diol is cycloalkyl substituted with one —OH and one —$R^P$—OH substituent. In some variations, the diol is $C_3$-$C_5$ cycloalkyl substituted with one —OH and one —$R^P$—OH substituent. In some variations, the diol is cycloalkyl substituted with two —$R^P$—OH substituents, wherein $R^P$ is independently alkyl. In some variations, the diol is $C_3$-$C_5$ cycloalkyl substituted with two —$R^P$—OH substituents, wherein $R^P$ is independently alkyl.

For example, in some variations, the diol is cyclopentane-1,3-diol.

In some variations, the diol is heterocycloalkyl, wherein the heterocycloalkyl is optionally substituted with one or more alkyl groups and is substituted with two substituents selected from the group consisting of —OH and —R$^p$—OH, wherein R$^p$ is alkyl. In some variation, the diol is heterocycloalkyl substituted with two hydroxyl groups. In certain variations, the diol is heterocycloalkyl substituted with one —OH and one —R$^p$—OH substituent. In some variations, the diol is heterocycloalkyl substituted with two —R$^p$—OH substituents, wherein R$^p$ is independently alkyl.

For example, in some variations, the diol is 2,5-bis(hydroxymethyl)tetrahydrofuran, (2,5-dihydrofuran-2,5-diyl)dimethanol, pyrrolidine-diyldimethanol, or 2,2'-(tetrahydrofuran-2,5-diyl)bis(ethan-1-ol).

In certain embodiments, the diol is tetrahydrofuranyl substituted with two —R$^p$—OH substituents, wherein R$^p$ at each instance is methyl. In one variation, the diol is:

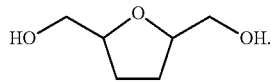

In some variations, the diol is aryl, wherein the aryl is optionally substituted with one or more alkyl groups and is substituted with two substituents selected from the group consisting of —OH and —R$^p$—OH, wherein R$^p$ is alkyl. In some variation, the diol is aryl substituted with two hydroxyl groups. In certain variations, the diol is aryl substituted with one —OH and one —R$^p$—OH substituent. In some variations, the diol is aryl substituted with two —R$^p$—OH substituents, wherein R$^p$ is independently alkyl.

For example, in some variations, the diol is hydroquinone, 4-(hydroxymethyl)phenol, or 1,4-phenylenedimethanol.

In some variations, the diol is heteroaryl, wherein the heteroaryl is optionally substituted with one or more alkyl groups and is substituted with two substituents selected from the group consisting of —OH and —R$^p$—OH, wherein R$^p$ is alkyl. In some variation, the diol is heteroaryl substituted with two hydroxyl groups. In certain variations, the diol is heteroaryl substituted with one —OH and one —R$^p$—OH substituent. In some variations, the diol is heteroaryl substituted with two —R$^p$—OH substituents, wherein R$^p$ is independently alkyl.

For example, in some variations, the diol is furan-2,5-diol, 5-(hydroxymethyl)furan-2-ol, or furan-2,5-diyldimethanol.

For example in some embodiments, the diol is furan substituted with two —OH groups. In certain embodiments, the diol is:

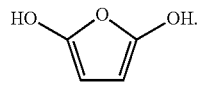

In other embodiments, the diol is furan substituted with two —R$^p$—OH substituents, wherein R$^p$ in each instance is methyl. In certain embodiments, the diol is:

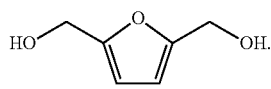

In some variations, the diol is ether, wherein the ether is optionally substituted with one or more alkyl groups and is substituted with two substituents selected from the group consisting of —OH and —R$^p$—OH, wherein R$^p$ is alkyl. In some variation, the diol is ether substituted with two hydroxyl groups. In certain variations, the diol is ether substituted with one —OH and one —R$^p$—OH substituent. In some variations, the diol is ether substituted with two —R$^p$—OH substituents, wherein R$^p$ is independently alkyl.

In some variations, the diol is of formula HO—A$^1$—OH, wherein A$^1$ is alkyl or —R$^p$—A$^2$—R$^p$—, wherein A$^2$ is cycloalkyl, heterocycloalkyl, aryl, heteroaryl, or ether, wherein the cycloalkyl, heterocycloalkyl, aryl, heteroaryl, or ether is optionally substituted with one or more alkyl groups, and each R$^p$ is independently alkyl.

For example, in some variations, the diol is of formula HO—A$^1$—OH, wherein A$^1$ is alkyl. In some variations, A$^1$ is linear alkyl. In certain variations, A$^1$ is methyl, ethyl, propyl, n-butyl, n-pentyl, n-hexyl, or n-heptyl.

In other variations, the diol is of formula HO—A$^1$—OH, wherein A$^1$ is:

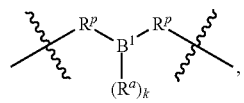

wherein:
each R$^a$ is independently H or alkyl; k is 2 or 6;

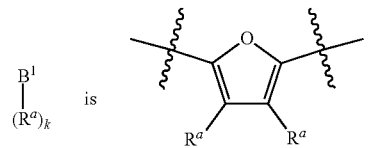

when k is 2;

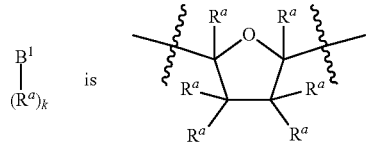

when k is 6; and each R$^p$ is independently -alkyl-.

For example, in some embodiments, k is 2. In other embodiments, k is 6. In certain embodiments, each R$^a$ is H. In other embodiments, at least one R$''$ is alkyl. In yet other embodiments, each R$^a$ is alkyl. In certain embodiments, each R$^p$ is -methyl-.

Prepolymer

As described above, in certain embodiments, a furan or tetrahydrofuran is combined with a diol in the presence of an organocatalyst to produce a prepolymer composition, or a furan or tetrahydrofuran is transesterified in the presence of an organocatalyst to produce a prepolymer composition, wherein the prepolymer composition comprises a prepolymer, and the prepolymer is polycondensed to produce a polymer composition.

In some embodiments, the prepolymer composition comprises one or more monomers or polymers that are capable of further polymerization reaction (including, for example, esterification and/or transesterification) to produce a polymer composition of a higher molecular weight. Thus, for example, in some embodiments the prepolymer composition comprises one or more of the furans/tetrahydrofurans, such as one or more compounds of formula (F), (F1), (F2), (G), (G1), or (G2), or diols described above.

For example, in some embodiments, the prepolymer composition comprises:

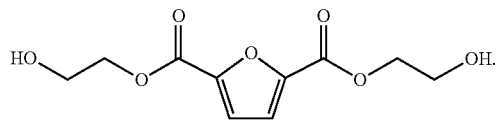 [SMILES: O=C(OCCO)c1ccc(C(=O)OCCO)o1]

In some embodiments, the prepolymer composition comprises one or more compounds of the following formula:

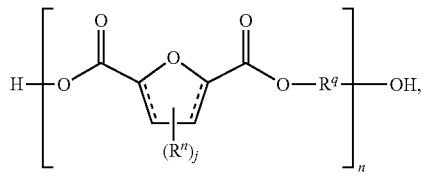

wherein:
=== is a double bond or a single bond;
j is 2 when === is a double bond, or j is 6 when === is a single bond j;
each $R''$ is independently H, aromatic or aliphatic;
$R^q$ is aromatic or aliphatic; and
n is an integer of 2 or greater.

In some variations, each $R''$ is independently H or alkyl. In some variations, $R^q$ is alkyl. In some embodiments, the prepolymer composition comprises one or more compounds of the following formula:

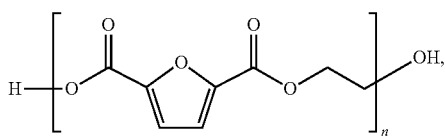

wherein n is an integer of 2 or greater.

As described above, a prepolymer composition can undergo further polymerization to produce a polymer composition with a higher molecular weight. In some embodiments, the prepolymer composition is further polymerized (such as esterified or transesterified) in the presence of an organocatalyst, and optionally in the presence of a solvent. The organocatalyst may be different or the same as the organocatalyst used to produce the prepolymer composition. In some embodiments, a furan or tetrahydrofuran is combined with a diol in the presence of an organocatalyst, or a furan or tetrahydrofuran is transesterified in the presence of an organocatalyst, to produce a prepolymer composition, and the prepolymer composition is isolated prior to further polymerization to produce the polymer composition. In other embodiments, the prepolymer composition is not isolated.

In other embodiments of the methods herein, a diol is not used in the reaction. Thus, in other variations, the furan or the tetrahydrofuran produces the polymer composition in the presence of an organocatalyst.

Organocatalysts

In some embodiments, the organocatalyst used in the methods described herein is a non-metal catalyst. In some embodiments, the organocatalyst is a non-transition metal catalyst.

In some variations, the organocatalyst comprises a carbene. In certain variations, the organocatalyst comprises a nitrogen-containing carbene. In certain embodiments, the organocatalyst is an N-heterocyclic carbene (NHC carbene). In some embodiments, the organocatalyst is an N-heterocyclic carbene comprising at least two heteroatoms selected from the group consisting of O, S, and N, wherein at least one heteroatom is N. In some embodiments, the N-heterocyclic carbene comprises two or three heteroatoms. In other embodiments, the organocatalyst is an acyclic heterocarbene comprising at least two heteroatoms selected from the group consisting of O, S, and N, wherein at least one heteroatom is N. In certain embodiments, the acyclic heterocarbene comprises two or three heteroatoms.

In some embodiments, the N-heterocyclic carbene is a compound of formula (C1):

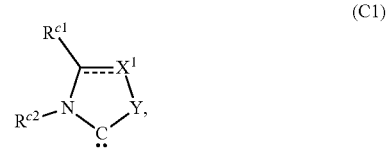

wherein:
$X^1$ is N, $CR_2$, or CR;
Y is $NR^{c3}$, O or S;
each R, if present, is independently H, aliphatic, or aromatic;
$R^{c1}$, $R^{c2}$, and $R^{c3}$ are independently H, aliphatic, or aromatic;
or wherein at least one R and $R^{c1}$, if present, are taken together with the atoms to which they are attached to form an aromatic or aliphatic cycle; and
=== is a single bond or a double bond.

As would be appreciated by those of ordinary skill in the art, N-heterocyclic carbenes can be synthesized using an imidazolium or triazolium precursor in the presence of a base. For example, 1-ethyl-3-methyl imidazolium chloride and/or 1,3-dimethylimidazolium chloride can be used as imidazolium precursors.

It should be understood that N-heterocyclic carbenes may also be described as:

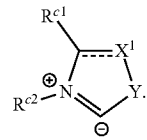

Exemplary N-heterocyclic carbenes include, but are not limited to,

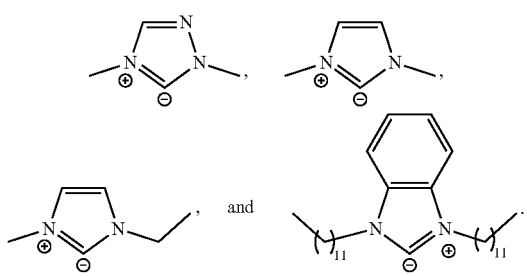

In some embodiments, the aliphatic is alkyl. In some embodiments, the aromatic is heteroaromatic. In one embodiment, each R is independently H or alkyl. In certain embodiments, $R^{c1}$, $R^{c2}$, and $R^{c3}$ are independently H or alkyl. In some variations, Y is $NR^{c3}$ or S. In certain variations, Y is $NR^{c3}$. In some variations, $R^{c1}$ and $R^{c2}$ are independently H or alkyl. In certain variations, $R^{c1}$ is H and $R^{c2}$ is alkyl. In some variations, the compound of formula (C1) is:

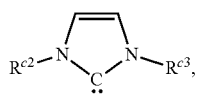

wherein $R^{c2}$ and $R^{c3}$ are independently H, aliphatic or aromatic.

It should be understood that the above compound may also be described as:

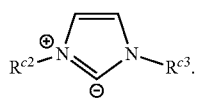

In some variations, $X^1$ is CR, wherein R is H; Y is $NR^{c3}$, wherein $R^{c3}$ is methyl; $R^{c2}$ is methyl; === is a single bond, and the compound of formula (C1) is:

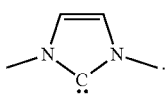

In some embodiments, the acyclic heterocarbene is a compound of formula (C2):

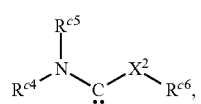

(C2)

wherein:

$X^2$ is $NR^{c7}$, O, or S; and $R^{c4}$, $R^{c5}$, $R^{c6}$, and $R^{c7}$ are independently H, aliphatic or aromatic.

In some embodiments, the aliphatic is alkyl. In certain embodiments, the aromatic is heteroaromatic. In certain embodiments, $R^{c4}$, $R^{c5}$, $R^{c6}$, and $R^{c7}$ are independently H or alkyl. In some embodiments, $R^{c4}$, $R^{c5}$, $R^{c6}$, and $R^{c7}$ are independently alkyl or aryl. In certain embodiments, $X^2$ is $NR^{c7}$.

In some embodiments, the organocatalyst is an optionally substituted imidazolium carbene, an optionally substituted azolium carbene, or an optionally substituted thiazolium carbene.

In some variations, the organocatalyst is produced in situ. For example, in some variations, the furan and the diol are combined to form a reaction mixture in the presence of an organocatalyst, wherein the organocatalyst is an N-heterocyclic carbene, wherein the N-heterocyclic carbene is produced in situ. In certain variations, a compound of formula (G) is transesterified to produce a polymer or mixture of polymers in the presence of an organocatalyst, wherein the organocatalyst is produced in situ.

In some variations, the organocatalyst is a salt, or is produced in situ from a salt. For example, in one variation, the organocatalyst is an N-heterocyclic carbene, wherein the N-heterocyclic carbene is produced from an N-heterocyclic salt. In one variation, the organocatalyst is an optionally substituted imidazolium carbene, an optionally substituted azolium carbene, or an optionally substituted thiazolium carbene produced from an optionally substituted imidazolium salt, an optionally substituted azolium salt, or an optionally substituted thiazolium salt, respectively. In some variations, the organocatalyst is a salt, or is produced from a salt, wherein the salt is a halide salt, for example, a chlorine salt, a fluorine salt, a bromine salt, or an iodine salt. Thus, in some embodiments the organocatalyst comprises a halide, for example, chloride, fluoride, bromide, or iodide, or mixtures thereof. Any combination of organocatalysts described herein may be employed.

Solvents

In some embodiments, the furan and the diol are combined in the presence of a solvent. In some variations, a compound of formula (G) is transesterified in the presence of an organocatalyst and a solvent. In some variations, the solvent comprises an ether. For example, in some variations, the solvent comprises tetrahydrofuran. In other variations, the solvent comprises a diol. For example, in some variations, a compound of formula (G) is transesterified in the presence of an organocatalyst and a diol, wherein the diol is as described above. Any combination or mixture of solvents described herein may be employed.

Polymer Composition

Provided are also compositions comprising the polymers described herein. In some variations, the composition comprises a polymer with a backbone, wherein the backbone comprises a furan or tetrahydrofuran moiety. For example, in some embodiments the backbone comprises a furandicarboxylate moiety, a tetrahydrofurandicarboxylate moiety, or a combination thereof. In some variations, the furan or tetrahydrofuran moiety may be unsubstituted or substituted. In certain variations, the backbone comprises an optionally substituted 2,5-furandicarboxylate moiety, or an optionally substituted 2,5-tetrahydrofurandicarboxylate moiety, or a combination thereof. It should be understood that the furan or tetrahydrofuran moiety in the backbone may be derived from one or more compounds of formulae (F), (F1), (F2), (G), (G1), or (G2) as described above. In some embodiments, the furan or tetrahydrofuran moiety is substituted, for example with one or more alkyl groups.

In some variations, the composition comprises a polymer with a backbone, wherein the backbone comprises a moiety of formula (P):

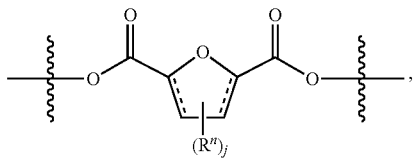

(P)

wherein:

=== is a double bond or a single bond;

j is 2 when === is a double bond, or j is 6 when === is a single bond j; and each $R''$ is independently H, aliphatic or aromatic.

In some variations, each $R''$ is independently H or alkyl. In some variations, === is a double bond, j is 2, and the moiety of formula (P) is a moiety of formula (P1):

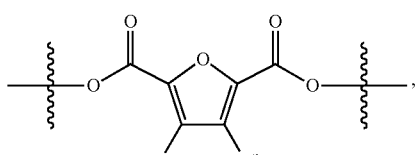

(P1)

wherein each $R''$ is independently H, aliphatic or aromatic.

In some variations, each $R''$ is independently H or alkyl. In some variations, === is a single bond, j is 6, and moiety of formula (P) is a moiety of formula (P2):

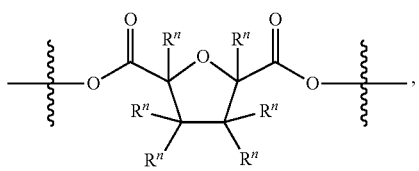

(P2)

wherein each $R''$ is independently H, aliphatic aromatic.

The moieties of formula (P), (P1) or (P2) are repeating units within the polymer. However, it should be understood that the polymer may include other moieties. In some variations, other moieties may be incorporated into the polymer backbone.

In some variations, each $R''$ is independently H or alkyl. The backbone may further comprises one or more alkylene moieties. In some embodiments, the alkylene moiety is derived from a diol, for example from a diol combined with a compound of formula (F) to produce the one or more polymers. In other embodiments, the alkylene moiety is derived from the compound of formula (G), for example from the $R^g$ groups present in the compound of formula (G).

Thus, in some embodiments, the composition comprises a polymer with a backbone, wherein the backbone comprises a moiety of formula (Q):

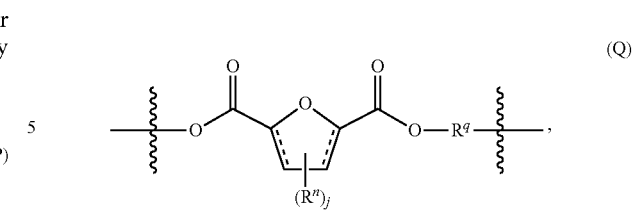

(Q)

wherein:

=== is a double bond or a single bond;

j is 2 when === is a double bond, or j is 6 when === is a single bond j;

each $R''$ is independently H, aliphatic or aromatic; and $R^q$ is aliphatic or aromatic.

In some variations, $R^q$ is alkyl. In some variations, each $R''$ is independently H or alkyl. In some variations, j is 2. In certain variations, $R''$ is H. In some variations, $R^q$ is ethyl, propyl, butyl, or pentyl. In one embodiment, $R^q$ is ethyl. It should be understood that in certain variations, the backbone comprises one or more moieties of formula (Q) wherein for each instance of the moiety, each of the variables j, $R''$, $R^q$, and === are independently selected. For example, in one embodiment, the backbone comprises at least two moieties of formula (Q), wherein in one moiety $R^q$ is ethyl and in another moiety $R^q$ is propyl, butyl, or pentyl.

For example, in one embodiment, the moiety of formula (Q) is:

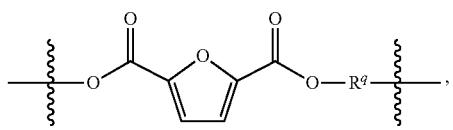

wherein $R^q$ is aliphatic or aromatic.

In some embodiments, $R^q$ is alkyl.

In one embodiment, the composition comprises a polymer backbone, wherein the polymer backbone comprises the moiety:

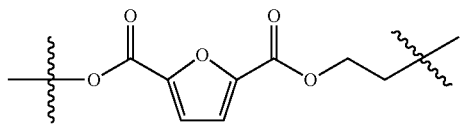

It should be understood that the backbone of the polymers described herein may comprise one or more different moieties of formula (P), (P1), (P2), or (Q), and/or the backbone may comprise one or more repeating units comprising a moiety of formula (P), (P1), (P2), or (Q).

In some embodiments, the backbone comprises a moiety of formula (P), (P1), (P2) or (Q), or a mixture of moieties of formula (P), (P1), (P2) or (Q), wherein the moiety or moieties are a repeating unit. For example, in some embodiments, the polymer composition comprises:

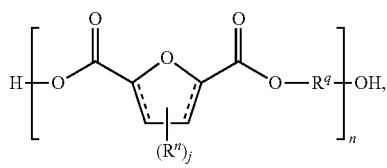

wherein:
=== is a double bond or a single bond;
j is 2 when === is a double bond, or j is 6 when === is a single bond j;
each $R^n$ is independently H, aliphatic or aromatic;
$R^q$ is aliphatic or aromatic; and
n is an integer of 2 or greater.

In some variations, $R^q$ is alkyl. In some variations, each $R^n$ is independently H or alkyl. As described above, in some embodiments the polymer comprises more than one repeating unit. Thus, in certain embodiments wherein the polymer composition comprises the above structure, the substituents j, $R^n$, $R^q$ and === for each repeating unit are independently selected.

In some variations, the polymer composition comprises:

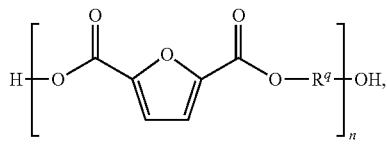

wherein $R^q$ is aromatic or aliphatic, and n is an integer of 2 or greater.

In some embodiments, $R^q$ is alkyl. In some aspects, the composition comprises poly(alkylene-2,5-furandicarboxylate). For example, in one aspect, the composition comprises poly(ethylene-2,5-furandicarboxylate).

In some aspects, the composition may be produced by any of the methods described herein, using any organocatalysts described herein. For example, in certain variations, the organocatalyst is a non-metal catalyst. In some variations, the organocatalyst is a non-transition metal catalyst, and non-lanthanoid metal catalyst, a non-post-transition metal catalyst, or a non-metalloid catalyst. In some variations, the organocatalyst exclude enzyme and acid chloride.

Provided herein is a polymer composition, wherein the polymer composition has one or more of the following characteristics: (1) organocatalyst residue; (2) antioxidant residue; (3) low metal content, such as a metal content lower than a polymer composition prepared with a metal catalyst; (4) no enzyme residue; (5) no acid chloride residue; (6) high molecular weight, such as a molecular weight of at least 10,000 Da (e.g., 10,000 Da-200,000 Da); and (7) low absorbance, such as an absorbance of less than 0.05 at 400 nm (e.g, 0.01-0.05 at 400 nm). It is understood that the compositions can have any one of the characteristics 1-7, or any combinations thereof, including all of characteristics 1-7.

In some embodiments, the polymer composition has a low metal content and a number average molecular weight of at least 10,000 Da, and a solution of 5 mg/mL of the polymer composition has an absorbance of less than 0.05 at 400 nm.

In some embodiments, the polymer composition has a low metal content and a nitrogen content that comes from organocatalysts used and have an number average molecular weight of at least 10,000 Da.

In some embodiments, the polymer composition comprises a residue from the N-heterocyclic carbene of formula (C1):

and has an number average molecular weight of at least 10,000 Da.

Organocatalyst Residue

In some variations, the polymer compositions herein comprise a residue from the organocatalyst. The residue from an organocatalyst may include the catalyst compound or derivatives thereof, or fragments of the catalyst compound used in the synthesis of the polymer.

The presence and/or amount of the organocatalyst residue may be measured by any suitable method known in the art, including, for example, gas chromatography—mass spectrometry (GC-MS), and nuclear magnetic resonance (NMR).

In some variations, the compositions provided herein, including polymer compositions produced according to the methods described herein, have a higher nitrogen content as compared to polymer compositions produced without an organocatalyst. In some variations, the polymer compositions herein comprise a nitrogen content that comes from organocatalysts used. In some embodiments, the nitrogen content is greater than 0.001 wt %, greater than 0.005 wt %, greater than 0.01 wt %, greater than 0.05 wt %, greater than 0.1 wt %, greater than 1 wt %, greater than 1.5 wt %, greater than 5 wt %, greater than 10 wt %, greater than 15 wt %, greater than 20 wt % or greater than 25 wt %. In some embodiments, the nitrogen content is in a range between 0.001 wt % to 1.5 wt %, between 0.0005 wt % to 5 wt %, or between 0.01 wt % to 15 wt %.

In some embodiments, the organocatalyst is an N-heterocyclic carbene (NHC carbene). In some embodiments, the polymer compositions herein comprise a residue from the N-heterocyclic carbene of formula (C1):

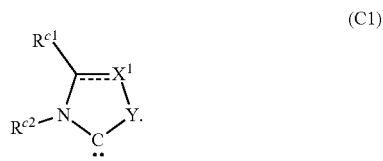

In some variations, the polymer compositions herein are free of a residue from the enzymes and/or acid chlorides. In some variations, the polymer compositions herein comprise a nitrogen content that does not comes from enzymes and acid chlorides. In some embodiments, the organocatalyst excludes enzymes and acid chlorides.

Antioxidant Residue

In some variation, the polymer compositions herein comprise a residue from the antioxidant compounds use according to the methods described herein. The residue from an antioxidant compound may include the antioxidant compound or derivatives thereof, or fragments of the antioxidant compound used in the synthesis of the polymer.

Metal Content

In some embodiments, the compositions provided herein, including polymer compositions produced according to the methods described herein, have a low metal content. In one variation, the metal content may include the content of metals and/or metalloids. In another variation, the metal content may include the content of metals and/or metalloids, but exclude the content of any alkali metals, alkaline earth metals, and silicon that may be present in the composition.

In some variations, the compositions provided herein, including polymer compositions produced according to the methods described herein, are free from metal catalysts. The metal catalysts may include, for example, catalysts used to produce the polymer. In some variations, such metal catalysts include metalloid catalysts.

In some embodiments, the compositions provided herein, including polymer compositions produced according to the methods described herein, have a metal content that does not come from catalysts used to produce the polymer. In one variation of the foregoing, catalysts that may be used to produce the polymer include transesterification catalysts. In certain variations, such transesterification catalyst may include tin, zirconium, hafnium, antimony, germanium, lead, titanium, bismuth, zinc, cadmium, aluminum manganese, cobalt, chromium, iron, tungsten, or vanadium, or any combinations thereof.

In certain variations, the compositions provided herein, including polymer compositions produced according to the methods described herein, are free from metals, including metalloids. In some variations, however, alkali metals, alkaline earth metals, and silicon may be present in the compositions. For example, alkali metals, alkaline earth metals, and silicon may be present in the composition in trace amounts.

In some variations, the compositions provided herein, including compositions produced according to the methods described herein, have less than 1 wt % metal, less than 0.5 wt % metal, less than 0.3 wt % metal, less than 0.1 wt % metal, less than 0.05 wt % metal, less than 0.04 wt % metal, less than 0.03 wt % metal, less than 0.02 wt % metal, less than 0.01 wt % metal, less than 0.009 wt % metal, less than 0.006 wt % metal, less than 0.003 wt % metal, less than 0.001 wt % metal, less than 0.0009 wt % metal, less than 0.0006 wt % metal, less than 0.0003 wt % metal, less than 0.0001 wt % metal, or less than 0.00009 wt % metal.

In some variations of the foregoing embodiments, the metal is a transition metal, or a heavy metal, or a combination thereof. In other variations, the metal is tin, zirconium, hafnium, antimony, or germanium, or any combinations thereof. In certain variations, the tin may be tin(IV) or tin(II), or a combination thereof. One or more metals may contribute to the metal content of the polymer composition.

In certain embodiments, the composition has a low content of one or more transition metals, one or more post-transition metals, one or more metalloids, or one or more lanthanoids, or any combinations thereof.

In some variations, the metal is one or more transition metals, one or more post-transition metals, one or more metalloids, one or more lanthanoid metals, or any combination thereof.

In certain embodiments, the total transition metal content of the composition is less than 1 wt %, less than 0.5 wt %, less than 0.3 wt %, less than 0.1 wt %, less than 0.05 wt %, less than 0.04 wt %, less than 0.03 wt %, less than 0.02 wt %, less than 0.01 wt %, less than 0.009 wt %, less than 0.006 wt %, less than 0.003 wt %, less than 0.001 wt %, less than 0.0009 wt %, less than 0.0006 wt %, less than 0.0003 wt %, less than 0.0001 wt %, or less than 0.00009 wt %. In some variations, the polymer composition has less than 0.09 wt % metal, less than 0.08 wt % metal, less than 0.07 wt % metal, less than 0.06 wt % metal, less than 0.05 wt % metal, less than 0.04 wt % metal, less than 0.03 wt % metal, or less than 0.02 wt % metal.

As described above, a transition metal may include an element of the d-block of the periodic table, including groups 3 to 12, and in some embodiments is scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, rutherfordium, dubnium, seaborgium, bohrium, hassium, meitnerium, darmstadtium, roentgenium, or copernicium.

As described above, a lanthanoid may include an element with an atomic number from 57 to 71, and in certain embodiments is lanthanum, cerium, praseodymium, neodymium, promethium, samarium, europium, gadolinium, terbium, dysprosium, holmium, erbium, thulium, ytterbium, or lutetium.

As described above, a post-transition metal may be gallium, indium, thallium, tin, lead, or bismuth.

As described above, a metalloid may be boron, silicon, germanium, arsenic, antimony, or tellurium.

In certain embodiments, the transition metal content, the lanthanoid metal content, the post-transition metal content, the metalloid content, or any combination thereof of the polymer composition is less than 1 mol %, less than 0.5 mol %, less than 0.3 mol %, less than 0.1 mol %, less than 0.05 mol %, less than 0.04 mol %, less than 0.03 mol %, less than 0.02 mol %, less than 0.01 mol %, less than 0.009 mol %, less than 0.006 mol %, less than 0.003 mol %, less than 0.001 mol %, less than 0.0009 mol %, less than 0.0006 mol %, less than 0.0003 mol %, less than 0.0001 mol %, or less than 0.00009 mol % relative to the compound of formula (G), which may include the furan or the tetrahydrofuran.

In some variations, the polymer composition has less than 400 ppm, less than 350 ppm, less than 300 ppm, less than 250 ppm, less than 200 ppm, less than 150 ppm, less than 100 ppm, less than 50 ppm, less than 25 ppm, less than 10 ppm, less than 8 ppm, less than 6 ppm, less than 5 ppm, less than 3 ppm, less than 1 wt %, less than 0.5 wt %, less than 0.3 wt %, less than 0.1 wt %, less than 0.05 wt %, less than 0.04 wt %, less than 0.03 wt %, less than 0.02 wt %, less than 0.01 wt %, less than 0.009 wt %, less than 0.006 wt %, less than 0.003 wt %, less than 0.001 wt %, less than 0.0009 wt %, less than 0.0006 wt %, less than 0.0003 wt %, less than 0.0001 wt %, or less than 0.00009 wt % of one or more of scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, rutherfordium, dubnium, seaborgium, bohrium, hassium, meitnerium, darmstadtium, roentgenium, copernicium, lanthanum, cerium, praseodymium, neodymium, promethium, samarium, europium, gadolinium, terbium, dysprosium, holmium, erbium, thulium, ytterbium, lutetium, gallium, indium, thallium, tin, lead, bismuth, boron, silicon, germanium, arsenic, antimony, or tellurium.

In some variations, the total content of scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, rutherfordium, dubnium, seaborgium, bohrium, hassium, meitnerium, darmstadtium, roentgenium, and copernicium in the polymer composition (if present) is less than 400 ppm, less than 350 ppm, less than 300 ppm, less than 250 ppm, less than 200 ppm, less than 150 ppm, less than 100 ppm, less than 50 ppm, less than 25 ppm, less than 10 ppm, less than 1 wt %, less than 0.5 wt %, less than 0.3 wt %, less than 0.1 wt %, less than 0.05 wt %, less than 0.04 wt %, less than 0.03 wt %, less than 0.02 wt %, less than 0.01 wt %, less than 0.009 wt %, less than 0.006 wt %, less than 0.003 wt %, less than 0.001 wt %, less than 0.0009 wt %, less than 0.0006 wt %, less than 0.0003 wt %, less than 0.0001 wt %, or less than 0.00009 wt %.

In some embodiments, the total content of lanthanum, cerium, praseodymium, neodymium, promethium, samarium, europium, gadolinium, terbium, dysprosium, holmium, erbium, thulium, ytterbium, and lutetium in the polymer composition (if present) is less than 400 ppm, less than 350 ppm, less than 300 ppm, less than 250 ppm, less than 200 ppm, less than 150 ppm, less than 100 ppm, less than 50 ppm, less than 25 ppm, less than 10 ppm, less than 1 wt %, less than 0.5 wt %, less than 0.3 wt %, less than 0.1 wt %, less than 0.05 wt %, less than 0.04 wt %, less than 0.03 wt %, less than 0.02 wt %, less than 0.01 wt %, less than 0.009 wt %, less than 0.006 wt %, less than 0.003 wt %, less than 0.001 wt %, less than 0.0009 wt %, less than 0.0006 wt %, less than 0.0003 wt %, less than 0.0001 wt %, or less than 0.00009 wt %.

In some embodiments, the total content of gallium, indium, thallium, tin, lead, and bismuth in the polymer composition (if present) is less than 400 ppm, less than 350 ppm, less than 300 ppm, less than 250 ppm, less than 200 ppm, less than 150 ppm, less than 100 ppm, less than 50 ppm, less than 25 ppm, less than 10 ppm, less than 1 wt %, less than 0.5 wt %, less than 0.3 wt %, less than 0.1 wt %, less than 0.05 wt %, less than 0.04 wt %, less than 0.03 wt %, less than 0.02 wt %, less than 0.01 wt %, less than 0.009 wt %, less than 0.006 wt %, less than 0.003 wt %, less than 0.001 wt %, less than 0.0009 wt %, less than 0.0006 wt %, less than 0.0003 wt %, less than 0.0001 wt %, or less than 0.00009 wt %.

In some embodiments, the total content of boron, silicon, germanium, arsenic, antimony, and tellurium in the polymer composition (if present) is less than 400 ppm, less than 350 ppm, less than 300 ppm, less than 250 ppm, less than 200 ppm, less than 150 ppm, less than 100 ppm, less than 50 ppm, less than 25 ppm, less than 10 ppm, less than 1 wt %, less than 0.5 wt %, less than 0.3 wt %, less than 0.1 wt %, less than 0.05 wt %, less than 0.04 wt %, less than 0.03 wt %, less than 0.02 wt %, less than 0.01 wt %, less than 0.009 wt %, less than 0.006 wt %, less than 0.003 wt %, less than 0.001 wt %, less than 0.0009 wt %, less than 0.0006 wt %, less than 0.0003 wt %, less than 0.0001 wt %, or less than 0.00009 wt %.

In some embodiments, the total content of aluminium, titanium, vanadium, chromium, manganese, iron, cobalt, zinc, geranium, zirconium, cadmium, tin, antimony, hafnium, tungsten, lead, and bismuth in the polymer composition (if present) is less than 400 ppm, less than 350 ppm, less than 300 ppm, less than 250 ppm, less than 200 ppm, less than 150 ppm, less than 100 ppm, less than 50 ppm, less than 25 ppm, less than 10 ppm, less than 1 wt %, less than 0.5 wt %, less than 0.3 wt %, less than 0.1 wt %, less than 0.05 wt %, less than 0.04 wt %, less than 0.03 wt %, less than 0.02 wt %, less than 0.01 wt %, less than 0.009 wt %, less than 0.006 wt %, less than 0.003 wt %, less than 0.001 wt %, less than 0.0009 wt %, less than 0.0006 wt %, less than 0.0003 wt %, less than 0.0001 wt %, or less than 0.00009 wt %.

In certain variations, the polymer composition has less than 400 ppm, less than 300 ppm, less than 200 ppm, less than 100 ppm, less than 50 ppm, less than 25 ppm, or less than 10 ppm of tin. In certain embodiments, the combination of transition metals and tin in the polymer composition is less than 400 ppm, less than 300 ppm, less than 200 ppm, less than 100 ppm, or less than 50 ppm.

In some variations, the polymer composition has a total transition metal content of less than 0.016 wt %, a total lanthanoid content of less than 0.01 wt %, a total post-transition metal content of less than 0.0075 wt %, and a total metalloid content of less than 0.02 wt %.

It should be understood that the metal contents described herein may be combined as if each and every combination were individually listed. For example, in one variation, the polymer composition has less than 0.000738 wt % of scandium, less than 0.000635 wt % of titanium, less than 0.000456 wt % of vanadium, less than 0.000265 wt % of chromium, less than 0.000145 wt % of manganese, less than 0.00130 wt % of iron, less than 0.000089 wt % of cobalt, less than 0.000380 wt % of nickel, less than 0.000104 wt % of copper, less than 0.00040 wt % of zinc, less than 0.000379 wt % of yttrium, less than 0.000442 wt % of zirconium, less than 0.000505 wt % of niobium, less than 0.000710 wt % of molybdenum, less than 0.000875 wt % of technetium, less than 0.000869 wt % of ruthenium, less than 0.001359 wt % of rhodium, less than 0.001391 wt % of palladium, less than 0.001273 wt % of silver, less than 0.001497 wt % of cadmium, less than 0.000197 wt % of hafnium, less than 0.000197 wt % of tantalum, less than 0.000223 wt % of tungsten, less than 0.000297 wt % of rhenium, less than 0.000190 wt % of osmium, less than 0.000212 wt % of iridium, less than 0.000249 wt % of platinum, less than 0.000243 wt % of gold, or less than 0.000282 wt % of mercury, or any combinations thereof.

In another variation, the polymer composition has less than 0.001998 wt % of lanthanum, less than 0.001440 wt % of cerium, less than 0.001161 wt % of praseodymium, less than 0.000929 wt % of neodymium, less than 0.00077 wt % of promethium, less than 0.00053 wt % of samarium, less than 0.00041 wt % of europium, less than 0.00038 wt % of gadolinium, less than 0.00037 wt % of terbium, less than 0.00042 wt % of dysprosium, less than 0.00025 wt % of holmium, less than 0.00025 wt % of erbium, less than 0.00022 wt % of thulium, less than 0.00027 wt % of ytterbium, or less than 0.00018 wt % of lutetium, or any combinations thereof.

In yet another variation, the polymer composition has less than 0.000078 wt % of gallium, less than 0.004280 wt % of indium, less than 0.002394 wt % of tin, less than 0.000299 wt % of lead, or less than 0.000330 wt % of bismuth, or any combinations thereof.

In yet another variation, the polymer composition has less than 0.01478 wt % of silicon, less than 0.000089 wt % of germanium, less than 0.00010 wt % of arsenic, less than 0.002701 wt % of antimony, or less than 0.002032 wt % of tellurium, or any combinations thereof.

In yet another variation, the polymer composition has less than 0.0026 wt % of aluminium, 0.00064 wt % of titanium, 0.00046 wt % of vanadium, 0.00027 wt % of chromium, 0.00015 wt % of manganese, 0.0014 wt % of iron, 0.00009 wt % of cobalt, 0.0004 wt % of zinc, 0.00009 wt % of geranium, 0.0004 wt % of zirconium, 0.0015 wt % of cadmium, 0.0024 wt % of tin, 0.0027 wt % of antimony, 0.00019 wt % of hafnium, 0.00022 wt % of tungsten, 0.00029 wt % of lead, or 0.00033 wt % of bismuth, or any combinations thereof.

In yet another variation, the polymer composition has less than 0.02 wt % of aluminium, 0.04 wt % of calcium, 0.06 wt % of copper, 0.02 wt % of magnesium, 0.05 wt % of manganese, 0.05 wt % of iron, 0.05 wt % of chromium, 0.05 wt % of zinc, or 0.05 wt % of nickel, or any combinations thereof.

In yet another variation, the polymer composition has about 0.0075 wt % of aluminium, about 0.0085 wt % of calcium, about 0.00014 wt % of copper, about 0.0214 wt % of magnesium, about 0.00034 wt % of manganese, about 0.0032 wt % of iron, about 0.00057 wt % of chromium, about 0.0020 wt % of zinc, or about 0.00021 wt % of nickel, or any combinations thereof.

In some variations, metal content of the polymer composition is the content of transition metals, lanthanoids, post-transition metals, or metalloids, or any combinations thereof, in the polymer composition. Any suitable methods or techniques known in the art to determine metal content may be employed.

It should be understood that a polymer composition with a certain level of metal content may comprise other levels of non-transition metals, non-lanthanoids, non-post-transition metals, or non-metalloids, or combinations thereof. For example, in some embodiments, the total content of transition metals in the polymer composition is less than 150 ppm, while the total content of alkali metals, alkaline earth metals, or a combination thereof is greater than 50 ppm, greater than 100 ppm, greater than 200 ppm, greater than 300 ppm, or greater than 400 ppm, In some variations, the total content of transition metals in the polymer composition is less than 150 ppm, while the total content of sodium, magnesium, or a combination thereof is greater than 50 ppm, greater than 75 ppm, greater than 100 ppm, greater than 150 ppm, or greater than 200 ppm.

In some variations the polymer composition has a metal content of less 0.025 wt %, wherein the metal content is based on Group II metals, transition metals, post-transition metals, metalloids, and/or lanthanoids (if present), provided that the metal content does not include the content of titanium or tin (if present).

In some variations the polymer composition has a metal content of less 0.02 wt %, wherein the metal content is based on Group II metals, transition metals, post-transition metals, metalloids, and/or lanthanoids (if present), provided that the metal content does not include the content of tin (if present).

In some variations the polymer composition has a metal content of less 0.003 wt %, wherein the metal content is based on transition metals, post-transition metals, metalloids, and/or lanthanoids (if present).

One or more metals may contribute to the metal content present in the polymer composition.

Color Content

Provided herein is also a polymer composition with low color content. The color content of a polymer composition may be determined by any suitable method known in the art. For example, the color of a polymer composition may be characterized by its absorbance value, measured by spectroscopy (e.g., UV spectroscopy).

In some embodiments, the color content of the polymer composition may be determined by absorbance of a 5 mg/mL solution of the polymer composition at a certain wavelength. In certain embodiments, the solution is 5 mg/mL of the polymer composition in a suitable solvent. In one embodiment the solution is 5 mg/mL of the polymer composition in hexafluoroisopropanol or hexafluoroisopropanol/DCM (2:8 ratio). In some embodiments, the absorbance of the solution is measured at a wavelength of 390 nm, 400 nm, 420 nm, 440 nm, 460 nm, 480 nm, 500 nm, 520 nm, 540 nm, 560 nm, 580 nm, 600 nm, 620 nm, 640 nm, 660 nm, 680 nm, or 700 nm. In certain embodiments, the polymer composition has an absorbance of less than 1, less than 0.5, less than 0.4, less than 0.3, less than 0.2, less than 0.1, less than 0.09, less than 0.08, less than 0.07, less than 0.06, less than 0.05, less than 0.04, less than 0.03, less than 0.02, less than 0.01, less than 0.009, less than 0.008, less than 0.007, less than 0.006, or less than 0.005.

In one embodiment, a solution of 5 mg/mL of the polymer composition in hexafluoroisopropanol has an absorbance of less than 0.05 at 400 nm.

Molecular Weight Characteristics

Polymers are comprised of a mixture of molecules possessing different molecular weights. This distribution in molecules arises from the polymerization process used to synthesize the polymer. Depending on the polymerization process and conditions, polymers can have molecular weight distributions which are polydisperse or monodisperse. There are three main average molecular weights used to characterize a polymer.

Number-Average Molecular Weight:

$$M_n = \frac{\sum_i N_i M_i}{\sum_i N_i}$$

Weight-Average Molecular Weight:

$$M_w = \frac{\sum_i N_i M_i^2}{\sum_i N_i M_i}$$

Z-Average Molecular Weight:

$$M_z = \frac{\sum_i N_i M_i^3}{\sum_i N_i M_i}$$

In some aspects, the polymer composition or prepolymer composition provided herein or produced by the methods described herein has a number average molecular weight (Mn) of at least 10,000 Daltons, at least 12,000 Daltons, at least 14,000 Dalton, at least 16,000 Daltons, at least 18,000 Daltons, at least 20,000 Daltons, at least 22,000 Daltons, at least 24,000 Daltons, at least 26,000 Daltons, at least 28,000 Daltons, at least 30,000 Daltons, at least 32,000 Daltons, at least 34,000 Daltons, at least 36,000 Daltons, at least 38,000 Daltons, at least 40,000 Daltons, at least 50,000 Daltons, at least 80,000 Daltons, at least 100,000 Daltons, at least 150,000 Daltons or at least 200,000 Daltons. In some embodiments, the polymer composition produced by the methods described herein has a Mn between 10,000 and 50,000 Daltons, between 10,000 and 40,000 Daltons, between 10,000 and 30,000 Daltons, between 10,000 and 20,000 Daltons, between 11,000 and 20,000 Daltons, between 12,000 and 20,000 Daltons, between 13,000 and 20,000 Daltons, between 14,000 and 20,000 Daltons, between 15,000 and 20,000 Daltons, between 10,000 and 25,000 Daltons, between 12,000 Daltons and 25,000 Daltons, between 14,000 Daltons and 25,000 Daltons, between 16,000 Daltons and 25,000 Daltons, between 18,000 Daltons and 25,000 Daltons, between 20,000 Daltons and 25,000 Daltons, between 15,000 and 50,000 Daltons, between 20,000 and 50,000 Daltons, between 25,000 and 50,000 Daltons, between 20,000 and 80,000 Daltons, between 50,000 and 80,000 Daltons, between 50,000 and 100,000 Daltons, between 80,000 and 100,000 Daltons, between 50,000 and 150,000 Daltons, between 80,000 and 150,000 Daltons, between 50,000 and 200,000 Daltons, between 80,000 and 200,000 Daltons, between 100,000 and 200,000 Daltons.

In some aspects, the polymer composition or prepolymer composition produced by the methods described herein has a weight average molecular weight ($M_w$) of at least 10,000 Daltons, at least 12,000 Daltons, at least 14,000 Dalton, at least 16,000 Daltons, at least 18,000 Daltons, at least 20,000 Daltons, at least 22,000 Daltons, at least 24,000 Daltons, at least 26,000 Daltons, at least 28,000 Daltons, at least 30,000 Daltons, at least 32,000 Daltons, at least 34,000 Daltons, at least 36,000 Daltons, at least 38,000 Daltons, at least 40,000 Daltons, at least 50,000 Daltons, at least 80,000 Daltons, at least 100,000 Daltons, at least 150,000 Daltons or at least 200,000 Daltons. In some embodiments, the polymer composition or prepolymer composition produced by the methods described herein has a $M_w$ between 10,000 and 50,000 Daltons, between 10,000 and 40,000 Daltons, between 10,000 and 30,000 Daltons, between 10,000 and 20,000 Daltons, between 11,000 and 20,000 Daltons, between 12,000 and 20,000 Daltons, between 13,000 and 20,000 Daltons, between 14,000 and 20,000 Daltons, between 15,000 and 20,000 Daltons, between 10,000 Daltons and 25,000 Daltons, between 12,000 Daltons and 25,000 Daltons, between 14,000 Daltons and 25,000 Daltons, between 16,000 Daltons and 25,000 Daltons, between 18,000 Daltons and 25,000 Daltons, between 20,000 Daltons and 25,000 Daltons, between 15,000 and 50,000 Daltons, between 20,000 and 50,000 Daltons, between 25,000 and 50,000 Daltons, between 20,000 and 80,000 Daltons, between 50,000 and 80,000 Daltons, between 50,000 and 100,000 Daltons, between 80,000 and 100,000 Daltons, between 50,000 and 150,000 Daltons, between 80,000 and 150,000 Daltons, between 50,000 and 200,000 Daltons, between 80,000 and 200,000 Daltons, between 100,000 and 200,000 Daltons.

The $M_w$ or $M_n$ may be measured by any suitable method known in the art, including, for example, gel-permeation chromatography (GPC), nuclear magnetic resonance (NMR), static light scattering, dynamic light scattering (DLS), or viscometry. For example, in some variations, the values of $M_w$ or $M_n$ described herein are determined based on NMR (see, e.g., the protocol in Izunobi, Josephat U. and Higginbotham, Clement L., Polymer Molecular Wight Analysis by $^1$H NMR Spectroscopy, Journal of Chemical Education, 2011, 88, 1098-1104

In certain embodiments, at least 50%, at least 60%, at least 70%, at least 80%, at least 90%, or at least 95% of the polymer composition or prepolymer composition has a molecular weight distribution between 10,000 and 50,000 Daltons, between 10,000 and 40,000 Daltons, between 10,000 and 30,000 Daltons, between 10,000 and 20,000 Daltons, between 11,000 and 20,000 Daltons, between 12,000 and 20,000 Daltons, between 13,000 and 20,000 Daltons, between 14,000 and 20,000 Daltons, between 15,000 and 20,000 Daltons, between 10,000 Daltons and 25,000 Daltons, between 12,000 Daltons and 25,000 Daltons, between 14,000 Daltons and 25,000 Daltons, between 16,000 Daltons and 25,000 Daltons, between 18,000 Daltons and 25,000 Daltons, between 20,000 Daltons and 25,000 Daltons, between 15,000 and 50,000 Daltons, between 20,000 and 50,000 Daltons, between 25,000 and 50,000 Daltons, between 20,000 and 80,000 Daltons, between 50,000 and 80,000 Daltons, between 50,000 and 100,000 Daltons, between 80,000 and 100,000 Daltons, between 50,000 and 150,000 Daltons, between 80,000 and 150,000 Daltons, between 50,000 and 200,000 Daltons, between 80,000 and 200,000 Daltons, between 100,000 and 200,000 Daltons.

A measure of the molecular weight distribution is the polydispersity index (PDI) which is the ratio of Mw over Mn. Molecular weight distribution of a polymer narrows as PDI values tend towards 1. In some variations, the polymer compositions provided herein, including polymer compositions produced according to the methods described herein, have a polydispersity index (PDI) of less than 4.0, less than 4.0, less than 3.5, less than 3.0, less than 2.5, less than 2.0, less than 1.5, or less than 1.25. In some variations, polymer composition provided herein or produced according to the methods described herein has a PDI between 1.0 and 4.0, between 2.0 and 4.0, between 3.0 and 4.0, between 1.0 and 3.0, or between 1.0 and 2.0. PDI may be measured using any suitable methods known in the art, including, for example, GPC, DLS, viscometry, or static light scattering.

In some variations, at least a portion of the one or more polymers in the polymer composition has a repeating unit, wherein the repeating unit is one furan monomer bonded to one diol monomer through an ester bond. In certain variations, the number of repeating units in a polymer is n. In some variations, the polymer composition has an average number of repeating units (n) of between 185 and 600. In some variations, the polymer composition has an average n of at least 185, at least 200, at least 225, at least 250, at least 275, at least 300, at least 325, at least 350, at least 375, at least 400, at least 425, at least 450, at least 475, at least 500, at least 525, at least 550, or at least 575. In some variations, the polymer composition has an average n of less than 600, less than 550, less than 500, less than 450, less than 400, less than 350, less than 300, less than 250, or less than 200.

In some embodiments, aliphatic as used herein has at least 2 carbon atoms (i.e., $C_{2+}$ aliphatic group), at least 3 carbon atoms (i.e., $C_{3+}$ aliphatic group), at least 4 carbon atoms (i.e., $C_{4+}$ aliphatic group), at least 5 carbon atoms (i.e., $C_{5+}$ aliphatic group), or at least 10 carbon atoms (i.e., $C_{10+}$ aliphatic group); or 1 to 40 carbon atoms (i.e., $C_{1-40}$ aliphatic group), 1 to 30 carbon atoms (i.e., $C_{1-30}$ aliphatic group), 1 to 25 carbon atoms (i.e., $C_{1-25}$ aliphatic group), 1 to 20 carbon atoms (i.e., $C_{1-20}$ aliphatic group), 5 to 20 carbon atoms (i.e., $C_{5-20}$ aliphatic group), or 14 to 18 carbon atoms (i.e., $C_{14-18}$ aliphatic group). The aliphatic group may be saturated or unsaturated (e.g., monounsaturated or polyunsaturated). Examples of saturated aliphatic groups include alkyl groups, such as methyl, ethyl, propyl and butyl. Examples of unsaturated aliphatic groups include alkenyl and alkynyl groups, such as ethenyl, ethynyl, propenyl, propynyl, butenyl, and butynyl.

As used herein, "alkyl" refers to a linear or branched saturated hydrocarbon chain. Examples of alkyl groups include methyl, ethyl, n-propyl, iso-propyl, n-butyl, sec-butyl, tert-butyl, n-pentyl, 2-pentyl, iso-pentyl, neo-pentyl, hexyl, 2-hexyl, 3-hexyl, and 3-methylpentyl. When an alkyl residue having a specific number of carbons is named, all geometric isomers having that number of carbons may be encompassed; thus, for example, "butyl" can include n-butyl, sec-butyl, iso-butyl and tert-butyl; "propyl" can include n-propyl and iso-propyl. In some embodiments, alkyl as used in the formulas and methods described herein has 1 to 40 carbon atoms (i.e., $C_{1-40}$), 1 to 30 carbon atoms (i.e., $C_{1-30}$ alkyl), 1 to 20 carbon atoms (i.e., $C_{1-20}$ alkyl), 1 to 15 carbon atoms (i.e., $C_{1-15}$ alkyl), 1 to 9 carbon atoms (i.e., $C_{1-9}$ alkyl), 1 to 8 carbon atoms (i.e., $C_{1-8}$ alkyl), 1 to 7 carbon atoms (i.e., $C_{1-7}$ alkyl), 1 to 6 carbon atoms (i.e., $C_{1-6}$ alkyl), 1 to 5 carbon atoms (i.e., $C_{1-5}$ alkyl), 1 to 4 carbon atoms (i.e., $C_{1-4}$ alkyl), 1 to 3 carbon atoms (i.e., $C_{1-3}$ alkyl), 1 to 2 carbon atoms (i.e., $C_{1-2}$ alkyl), or 1 carbon atom (i.e., $C_1$ alkyl).

"Alkenyl" as used herein refers to an unsaturated linear or branched univalent hydrocarbon chain or combination thereof, having at least one site of olefinic unsaturation (i.e., having at least one moiety of the formula C=C) and having the number of carbon atoms designated (i.e., $C_2$-$C_{10}$ means two to ten carbon atoms). The alkenyl group may be in "cis" or "trans" configurations, or alternatively in "E" or "Z" configurations. Particular alkenyl groups are those having 2 to 20 carbon atoms (a "$C_2$-$C_{20}$ alkenyl"), having 2 to 8 carbon atoms (a "$C_2$-$C_8$ alkenyl"), having 2 to 5 carbon atoms (a "$C_2$-$C_5$ alkenyl"), or having 2 to 4 carbon atoms (a "$C_2$-$C_4$ alkenyl"). Examples of alkenyl include, but are not limited to, groups such as ethenyl (or vinyl), prop-1-enyl, prop-2-enyl (or allyl), 2-methylprop-1-enyl, but-1-enyl, but-2-enyl, but-3-enyl, buta-1,3-dienyl, 2-methylbuta-1,3-dienyl, homologs and isomers thereof, and the like.

"Aryl" refers to an aromatic carbocyclic group having a single ring (e.g., phenyl), multiple rings (e.g., biphenyl), or multiple fused rings (e.g., naphthyl, fluorenyl, and anthryl). In certain embodiments, aryl as used herein has 6 to 20 ring carbon atoms (i.e., $C_{6-20}$ aryl), or 6 to 12 carbon ring atoms (i.e., $C_{6-12}$ aryl). Aryl, however, does not encompass or overlap in any way with heteroaryl, separately defined below. In certain embodiments, if one or more aryl groups are fused with a heteroaryl ring, the resulting ring system is heteroaryl.

"Heteroaryl" refers to an aromatic group having a single ring, multiple rings, or multiple fused rings, with one or more ring heteroatoms independently selected from nitrogen, oxygen, and sulfur. In some embodiments, heteroaryl is an aromatic, monocyclic or bicyclic ring containing one or more heteroatoms independently selected from nitrogen, oxygen and sulfur with the remaining ring atoms being carbon. In certain embodiments, heteroaryl as used herein has 3 to 20 ring carbon atoms (i.e., $C_{3-20}$ heteroaryl). 3 to 12 ring carbon atoms (i.e., $C_{3-12}$ heteroaryl), or 3 to 8 carbon ring atoms (i.e., $C_{3-8}$ heteroaryl); and 1 to 5 heteroatoms, 1 to 4 heteroatoms, 1 to 3 ring heteroatoms, 1 or 2 ring heteroatoms, or 1 ring heteroatom independently selected from nitrogen, oxygen, and sulfur. In one example, a heteroaryl has 3 to 8 ring carbon atoms, with 1 to 3 ring heteroatoms independently selected from nitrogen, oxygen and sulfur. Examples of heteroaryl groups include pyridyl, pyridazinyl, pyrimidinyl, benzothiazolyl, and pyrazolyl. Heteroaryl does not encompass or overlap with aryl as defined above.

ENUMERATED EMBODIMENTS

The following enumerated embodiments are representative of some aspects of the invention.

1. A method of producing a polymer composition, comprising:
    a) combining a furan with a diol in the presence of an organocatalyst, wherein:
        the furan is optionally substituted furan-2,5-dicarboxylic acid, optionally substituted furan-2,5-dicarboxylic acid dialkyl ester, optionally substituted tetrahydrofuran-2,5-dicarboxylic acid, or optionally substituted tetrahydrofuran-2,5-dicarboxylic acid dialkyl ester; and
        the diol is alkyl, cycloalkyl, heterocycloalkyl, aryl, heteroaryl, or ether,
            wherein the cycloalkyl, heterocycloalkyl, aryl, heteroaryl, or ether is optionally substituted with one or more alkyl groups, and is substituted with two substituents independently selected from the group consisting of —OH and —$R^p$—OH, wherein $R^p$ is alkyl; and
    b) esterifying at least a portion of the furan with at least a portion of the diol to produce the polymer composition,
        wherein a solution of 5 mg/mL of the polymer composition in hexafluoroisopropanol has an absorbance of less than 0.05 at 400 nm.

2. A method of producing a polymer composition, comprising:
    a) combining a furan with a diol in the presence of an organocatalyst, wherein:
        the furan is optionally substituted furan-2,5-dicarboxylic acid, optionally substituted furan-2,5-dicarboxylic acid dialkyl ester, optionally substituted tetrahydrofuran-2,5-dicarboxylic acid, or optionally substituted tetrahydrofuran-2,5-dicarboxylic acid dialkyl ester; and
        the diol is alkyl, cycloalkyl, heterocycloalkyl, aryl, heteroaryl, or ether,
            wherein the cycloalkyl, heterocycloalkyl, aryl, heteroaryl, or ether is optionally substituted with one or more alkyl groups, and is substituted with two substituents independently selected from the group consisting of —OH and —$R^p$—OH, wherein $R^p$ is alkyl;
    b) esterifying at least a portion of the furan with at least a portion of the diol to produce a prepolymer composition; and
    c) polycondensing at least a portion of the prepolymer composition to produce the polymer composition,
        wherein a solution of 5 mg/mL of the polymer composition in hexafluoroisopropanol has an absorbance of less than 0.05 at 400 nm.

3. A method of producing a polymer composition, comprising:
    a) combining a furan with a diol in the presence of a first organocatalyst, wherein:
        the furan is optionally substituted furan-2,5-dicarboxylic acid, optionally substituted furan-2,5-dicarboxylic acid dialkyl ester, optionally substituted tetrahydrofuran-2,5-dicarboxylic acid, or optionally substituted tetrahydrofuran-2,5-dicarboxylic acid dialkyl ester; and
        the diol is alkyl, cycloalkyl, heterocycloalkyl, aryl, heteroaryl, or ether,
            wherein the cycloalkyl, heterocycloalkyl, aryl, heteroaryl, or ether is optionally substituted with one or more alkyl groups, and is substituted with two substituents independently selected from the group consisting of —OH and —$R^p$—OH, wherein $R^p$ is alkyl;
    b) esterifying at least a portion of the furan with at least a portion of the diol to produce a prepolymer composition;

c) polycondensing at least a portion of the prepolymer composition to produce a polymer condensate composition; and d) drying and/or crystallizing the polymer condensate composition to produce the polymer composition, wherein a solution of 5 mg/mL of the polymer composition in hexafluoroisopropanol has an absorbance of less than 0.05 at 400 nm.

4. The method of embodiment 2 or 3, wherein the prepolymer composition is polycondensed in the presence of a catalyst.

5. The method of embodiment 4, wherein the catalyst is the organocatalyst.

6. The method according to any one of embodiments 1 to 5, wherein combining the furan with the at least one diol forms a reaction mixture.

7. The method according to embodiment 6, wherein the reaction mixture comprises less than 0.2 mol % metal relative to the furan.

8. The method according to embodiment 7, wherein the reaction mixture comprises less than 0.01 mol % metal relative to the furan.

9. The method according to any one of embodiments 1 to 8, wherein the polymer composition comprises less than 1 wt % metal.

10. The method according to any one of embodiments 1 to 9, wherein the polymer composition comprises less than 0.1 wt % metal.

11. The method according to any one of embodiments 1 to 10, wherein the prepolymer composition comprises less than 1 wt % metal.

12. The method according to any one of embodiments 1 to 10, wherein the prepolymer composition comprises less than 0.1 wt % metal.

13. The method according to any one of embodiments 3 to 12, wherein the polymer condensate composition comprises less than 1 wt % metal.

14. The method according to any one of embodiments 3 to 12, wherein the polymer condensate composition comprises less than 0.1 wt % metal.

15. The method according to any one of embodiments 1 to 14, wherein the polymer composition has a number average molecular weight of at least 10,000 Da.

16. The method according to any one of embodiments 1 to 14, wherein the polymer composition has a number average molecular weight of at least 20,000 Da.

17. The method according to any one of embodiments 1 to 16, wherein the furan is of formula (I):

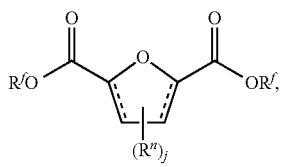

(I)

wherein:
each $R^n$ is independently H or alkyl;
each $R^f$ is independently H or alkyl;
=== is a double bond or a single bond; and
j is 2 when === is a double bond, or j is 6 when === is a single bond.

18. The method according to embodiment 17, wherein each $R^n$ is H.

19. The method according to embodiment 17 or 18, wherein each $R^f$ is independently H or C1-C6 alkyl.

20. The method according to any one of embodiments 1 to 19, wherein the diol is HO—$A^1$—OH, wherein $A^1$ is:
(i) alkyl, or
(ii)

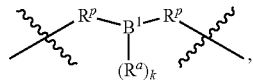

wherein:
each $R^a$ is independently H or alkyl;
k is 2 or 6;
$B^1$ is

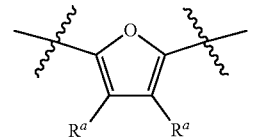

when k is 2;
$B^1$ is

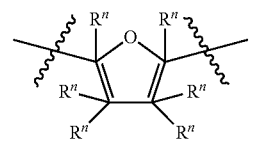

when k is 6; and
each $R^p$ is independently -alkyl-.

21. The method according to embodiment 20, wherein $A^1$ is alkyl.

22. The method according to embodiment 20 or 21, wherein $A^1$ is C2-C8 alkyl.

23. The method according to any one of embodiments 1 to 22, wherein the furan is 2,5-furandicarboxylic acid or 2,5-tetrahydrofurandicarboxylic acid.

24. The method according to any one of embodiments 1 to 23, wherein the diol is selected from the group consisting of ethane-1,2-diol, propane-1,3-diol, butane-1,4-diol, pentane-1,5-diol, hexane-1,6-diol, pentane-1,7-diol, and octane-1,8-diol.

25. The method according to any one of embodiments 1 to 24, wherein the furan and the diol are combined in the presence of a solvent.

26. The method according to embodiment 25, wherein the solvent is tetrahydrofuran.

27. The method according to any one of embodiments 1 to 26, wherein the organocatalyst is a non-metal catalyst.

28. The method according to any one of embodiments 1 to 27, wherein the organocatalyst is an N-heterocyclic carbene.

29. The method according to embodiment 28, wherein the N-heterocyclic carbene is produced in situ.

30. A polymer composition produced according to the method of any one of embodiments 1 to 29.

31. A polymer composition, wherein the polymer is poly(alkylene-2,5-furandicarboxylate) or poly(alkylene-2,5-tetrahydrofurandicarboxylate), comprising less than 1 wt % metal, and wherein a solution of 5 mg/mL of the polymer composition in hexafluoroisopropanol has an absorbance of less than 0.05 at 400 nm.
32. The polymer composition of embodiment 30 or 31, comprising less than 0.1 wt % metal.
33. The polymer composition of embodiment 30 to 32, comprising less than 0.01 wt % metal.
34. The polymer composition of any one of embodiments 30 to 33, wherein the polymer is poly(ethylene-2,5-furandicarboxylate), poly(propylene-2,5-furandicarboxylate), or poly(butylene-2,5-furandicarboxylate).
35. The polymer composition of any one of embodiments 30 to 33, wherein the polymer is poly(ethylene-2,5-tetrahydrofurandicarboxylate), poly(propylene-2,5-tetrahydrofurandicarboxylate), or poly(butylene-2,5-tetrahydrofurandicarboxylate).
36. The polymer composition of any one of embodiments 30 to 35, wherein the polymer composition has a number average molecular weight of at least 10,000 Da.
37. The polymer composition of any one of embodiments 30 to 36, wherein the polymer composition has a number average molecular weight of at least 20,000 Da.
38. The method of any one of embodiments 2 to 29, wherein: the prepolymer composition comprises

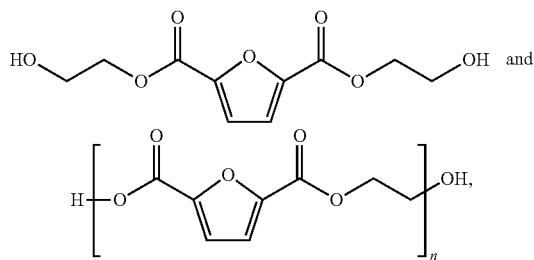

wherein n is an integer of 2 or greater;
the polymer composition comprises

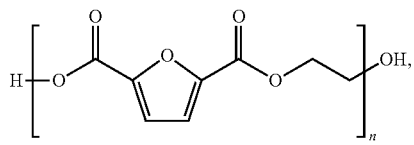

wherein n is an integer of 3 or greater; and
wherein the molecular weight of the polymer composition is greater than the molecular weight of the prepolymer composition.
39. A composition comprising a polymer with a polymer backbone, wherein the polymer backbone comprises an optionally substituted furandicarboxylate moiety or an optionally substituted tetrahydrofurandicarboxylate moiety,
wherein the composition is free from metal catalysts or residues thereof, and
wherein a solution of 5 mg/mL of the polymer composition in hexafluoroisopropanol has an absorbance of less than 0.05 at 400 nm.
40. A composition comprising a polymer with a polymer backbone, wherein the polymer backbone comprises an optionally substituted furandicarboxylate moiety or an optionally substituted tetrahydrofurandicarboxylate moiety,
wherein the composition has a metal content that does not come from metal catalysts used to produce the polymer or precursors thereof, and
wherein a solution of 5 mg/mL of the polymer composition in hexafluoroisopropanol has an absorbance of less than 0.05 at 400 nm.
41. The composition of embodiment 39 or 40, wherein the metal catalysts are transesterification catalysts.
42. A composition comprising a polymer with a polymer backbone, wherein the polymer backbone comprises an optionally substituted furandicarboxylate moiety or an optionally substituted tetrahydrofurandicarboxylate moiety,
wherein the composition is free from metal catalysts or residues thereof, and
wherein a solution of 5 mg/mL of the polymer composition in hexafluoroisopropanol has an absorbance of less than 0.05 at 400 nm.
43. A composition comprising a polymer with a polymer backbone, wherein the polymer backbone comprises an optionally substituted furandicarboxylate moiety or an optionally substituted tetrahydrofurandicarboxylate moiety,
wherein the composition has a total metal content of less than 0.1 wt %, and
wherein a solution of 5 mg/mL of the polymer composition in hexafluoroisopropanol has an absorbance of less than 0.05 at 400 nm.
44. The composition of any one of embodiments 39 to 43, wherein the composition has an number average molecular weight of at least 10,000 Da.
45. The composition of embodiment 43 or 44, wherein: (i) the total metal content includes the content of transition metals, post-transition metals, metalloids, or lanthanoid metals, or any combinations thereof; or (ii) the total metal content excludes the content of alkali metals, alkaline earth metals, and silicon, or a combination of (i) and (ii).
46. The composition of any one of embodiments 39 to 45, wherein the optionally substituted furandicarboxylate moiety is an optionally substituted 2,5-furandicarboxylate moiety, and the optionally substituted tetrahydrofurandicarboxylate moiety is an optionally substituted 2,5-tetrahydrofurandicarboxylate moiety.
47. The composition of any one of embodiments 39 to 46, wherein the optionally substituted furandicarboxylate moiety is:

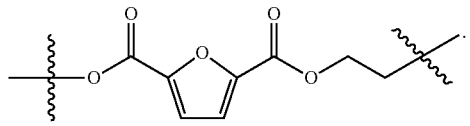 [SMILES: *CCOC(=O)c1ccc(C(=O)O*)o1]

48. The composition of any one of embodiments 39 to 47, wherein the polymer is poly(alkylene-2,5-furandicarboxylate) or poly(alkylene-2,5-tetrahydrofurandicarboxylate).
49. The composition of embodiment 48, wherein the polymer is poly(ethylene-2,5-furandicarboxylate) or poly(ethylene-2,5-tetrahydrofurandicarboxylate).
50. The composition of any one of embodiments 39 to 49, further comprising an organocatalyst.
51. The composition of embodiment 50, wherein the organocatalyst is a non-transition metal catalyst, a non-post-transition metal catalyst, a non-metalloid catalyst, or a non-lanthanoid catalyst, or any combinations thereof.

52. The composition of embodiment 50, wherein the organocatalyst is an N-heterocyclic carbene.

53. The composition of embodiment 50, wherein the organocatalyst comprises optionally substituted imidazolium carbene, an optionally substituted azolium carbene, or an optionally substituted thiazolium carbene.

54. The composition of embodiment 50, wherein the organocatalyst is a compound of formula (C1):

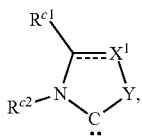

wherein:
$X^1$ is N, $CR_2$, or CR;
Y is $NR^{c3}$, O or S;
each R, if present, is independently H, aliphatic or aromatic;
$R^{c1}$, $R^{c2}$, and $R^{c3}$ are independently H, aliphatic or aromatic; and
=== is a single bond or a double bond.

55. The composition of embodiment 50, wherein the organocatalyst comprises:

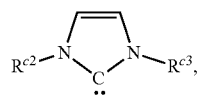

wherein $R^{c2}$ and $R^{c3}$ are independently H, aliphatic or aromatic.

56. The composition of embodiment 50, wherein each $R^{c2}$ and $R^{c3}$ is independently alkyl.

57. A method, comprising polymerizing a furan or tetrahydrofuran in the presence of an organocatalyst to produce a polymer composition,
wherein the furan or tetrahydrofuran is a compound of formula (G):

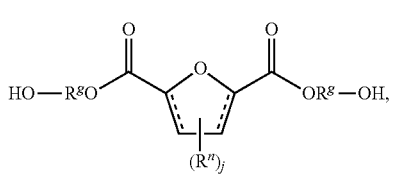

wherein:
=== is a double bond or a single bond;
j is 2 when === is a double bond, or j is 6 when === is a single bond j;
each $R^n$ is independently H or alkyl; and
each $R^g$ is independently alkyl, and
wherein the polymer composition comprises a polymer with a polymer backbone, wherein the polymer backbone comprises a moiety of formula (Q'):

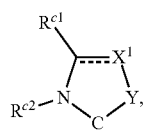

wherein ===, j is 2, $R^n$ and $R^g$ are as defined above for formula (G), and
wherein a solution of 5 mg/mL of the polymer composition in hexafluoroisopropanol has an absorbance of less than 0.05 at 400 nm.

58. The method of embodiment 57, wherein the organocatalyst is generated in situ.

59. The method of embodiment 57 or 58, wherein the organocatalyst is a non-transition metal catalyst, a non-post-transition metal catalyst, a non-metalloid catalyst, or a non-lanthanoid catalyst, or any combinations thereof.

60. The method of embodiment 57 or 58, wherein the organocatalyst is an N-heterocyclic carbene.

61. The method of embodiment 57 or 58, wherein the organocatalyst comprises optionally substituted imidazolium carbene, an optionally substituted azolium carbene, or an optionally substituted thiazolium carbene.

62. The method of embodiment 57 or 58, wherein the organocatalyst is a compound of formula (C1):

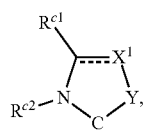

wherein:
$X^1$ is N, $CR_2$, or CR;
Y is $NR^{c3}$, O or S;
each R, if present, is independently H, aliphatic or aromatic;
$R^{c1}$, $R^{c2}$, and $R^{c3}$ are independently H, aliphatic or aromatic; and
=== is a single bond or a double bond.

63. The method of embodiment 57 or 58, wherein the organocatalyst comprises:

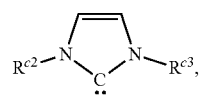

wherein $R^{c2}$ and $R^{c3}$ are independently H, aliphatic or aromatic.

64. The method of embodiment 63, wherein each $R^{c2}$ and $R^{c3}$ is independently alkyl.

65. The method of any one of embodiments 57 to 64, wherein the compound of formula (G) is:

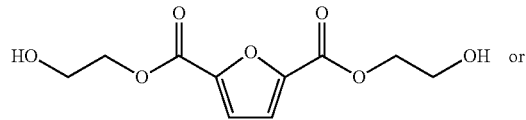 or

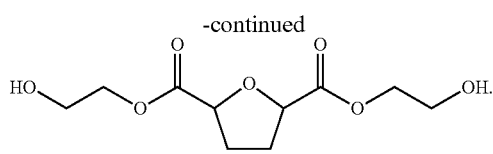

66. The method of any one of embodiments 57 to 65, wherein the polymer is a poly(alkylene-2,5-furandicarboxylate), or a poly(alkylene-2,5-tetrahydrofurandicarboxylate).
67. The method of embodiment 66, wherein the polymer is poly(ethylene-2,5-furandicarboxylate) or poly(ethylene-2,5-tetrahydrofurandicarboxylate).
68. A polymer composition produced according to the method of any one of embodiments 57 to 67.
69. A composition, comprising:
a compound of formula (G):

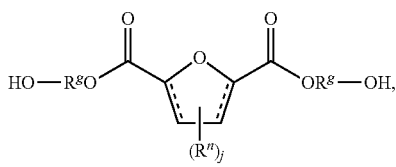

wherein:
=== is a double bond or a single bond;
j is 2 when === is a double bond, or j is 6 when === is a single bond j;
each $R^n$ is independently H or alkyl; and
each $R^g$ is independently alkyl; and
an organocatalyst,
wherein a solution of 5 mg/mL of the composition in hexafluoroisopropanol has an absorbance of less than 0.05 at 400 nm.
70. The composition of embodiment 69, wherein the organocatalyst is a non-transition metal catalyst, a non-post-transition metal catalyst, a non-metalloid catalyst, or a non-lanthanoid catalyst, or any combinations thereof.
71. The composition of embodiment 69, wherein the organocatalyst is an N-heterocyclic carbene.
72. The composition of embodiment 69, wherein the organocatalyst comprises optionally substituted imidazolium carbene, an optionally substituted azolium carbene, or an optionally substituted thiazolium carbene.
73. The composition of embodiment 69, wherein the organocatalyst is a compound of formula (C1):

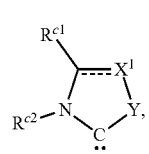

wherein:
$X^1$ is N, $CR_2$, or CR;
Y is $NR^{c3}$, O or S;
each R, if present, is independently H, aliphatic or aromatic;
$R^{c1}$, $R^{c2}$, and $R^{c3}$ are independently H, aliphatic or aromatic; and
=== is a single bond or a double bond.
74. The composition of embodiment 69, wherein the organocatalyst comprises:

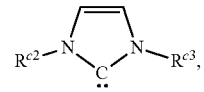

wherein $R^{c2}$ and $R^{c3}$ are independently H, aliphatic or aromatic.
75. The composition of embodiment 74, wherein each $R^{c2}$ and $R^{c3}$ is independently alkyl.
76. The composition of any one of embodiments 69 to 75, wherein the compound of formula (G) is:

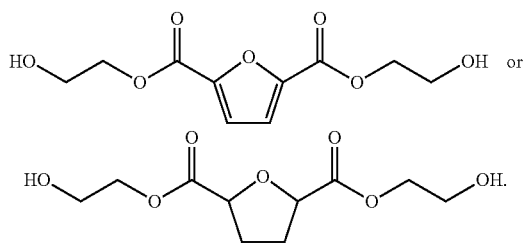

77. The composition of any one of embodiments 69 to 76, further comprising a solvent.
78. The composition of any one of embodiments 69 to 75, further comprising a polymer with a polymer backbone, wherein the polymer backbone comprises a moiety of formula (Q'):

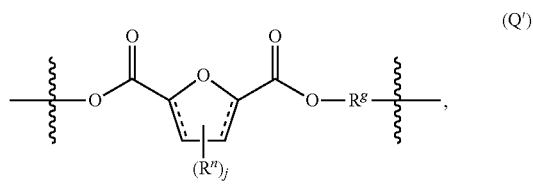

wherein ===, j is 2, $R^n$ and $R^g$ are as defined above for formula (G).
79. The composition of embodiment 78, wherein the polymer is a poly(alkylene-2,5-furandicarboxylate), or a poly(alkylene-2,5-tetrahydrofurandicarboxylate).
80. The composition of embodiment 78, wherein the polymer is poly(ethylene-2,5-furandicarboxylate) or poly(ethylene-2,5-tetrahydrofurandicarboxylate).

EXAMPLES

The following Examples are merely illustrative and are not meant to limit any aspects of the present disclosure in any way.

UV Absorbance

A 5 mg/ml solution of a polymer in hexafluoroisopropanol was made and its absorbance was measured at 400 nm.

Particle-Induced X-ray Emission (PIXE)

The PIXE system is composed of a General Ionex 4 MV tandem accelerator with a duoplasmatron source capable of producing beam currents in the range of a few nanoamps to tens of microamps, a dual quadrapole focusing lens, an x-y beam scanner to insure beam homogeneity, a beam pulser with 50 ns response time and a vacuum/helium chamber with internal dimensions of 20"w×16"l×8"h. The data acquisition system consists of a combination of an AT style computer which drives a CAMAC crate front ended with a 150 eV resolution, 30 mm$^2$ Si(Li) detector for X-ray collection and Au surface barrier detector to monitor scattered protons. Data reduction is accomplished with software developed at the University of Guelph and modified for use here. Data reduction and storage are performed with a data link to several 486 computers.

Gel Permeation Chromatography (GPC)

The instrument used for all SEC/GPC analysis consists of a Viscotek SEC/GPCmax Integrated Pump, Autosampler and Degasser unit and a Viscotek Triple Detection Array Model 302 (TDA302) equipped with an oven that houses four detectors (Refractive Index (RI), Ultra-Violet (UV), Right Angle and Low Angle Light Scattering (RALS/LALS), and Four-Capillary Differential Viscometer. Data was processed with the OmniSEC software 4.6.2 Build 359 (Malvern Instruments).

PEF samples were dissolved in the mobile phase at 3 mg/mL. Samples were left to dissolve overnight while rocking on a rocker at room temperature followed by 30 min of sonication. The dissolved polymer solution was filtered through 0.45 μm PTFE syringe filter into a GPC autosampler vial and 100 μL was injected into the calibrated GPC system.

Example 1

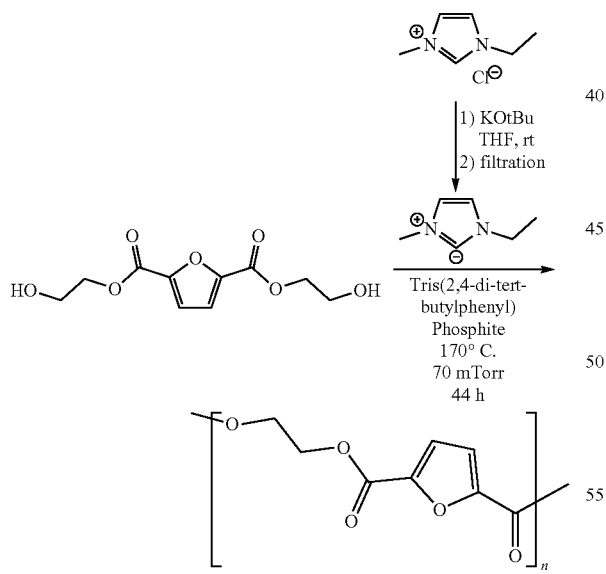

Inside an Argon-charged glove bag, 1-ethyl-3-methyl imidazolium chloride (0.051 eq), sublimed potassium tert-butoxide (0.06 eq) and anhydrous THF (0.034 M with imidazolium precursor) were added to a 3-neck flame dried round bottom flask equipped with a stir bar. Then this reaction mixture was taken out of the glove bag and put under inert gas while being stirred for 20 min at 25° C. Then this mixture was moved back inside the Argon-charged glove bag and it was filtered through a 0.45 μm filter into a flame-dried 3 neck round bottom flask equipped with a stir bar and containing bis(2-hydroxyethyl) furan-2,5-dicarboxylate (1 eq) and Tris(2,4-di-tert-butylphenyl) Phosphite (0.225 mol %). This reaction flask was taken out of the glove bag and stirred for 10 min at 25° C. under inert gas until a solid was suspended. Then the THF was vacuumed off slowly to prevent splashing. Once only solids remained, the round bottom flask was immersed in an oil bath at room temperature and it was heated gradually to 170° C. (oil bath temp) while under vacuum. Once the desired temperature was reached, it was held at this temp for 44 h under vacuum (70 mtorr). The reaction flask was then cooled down to room temperature and was moved into an Argon-charged glove bag. The contents of the flask were then scratched off with a spatula and transferred into a flame dried 3 neck Morton indented flask and placed on a rotovap at 1 rotation per sec and immersed in an oil bath at 180° C. under vacuum (3-5 torr) for solid state polymerization (total time 131 h). After 84 h of SSP, 0.04 eq of NHC carbene dissolved in THF was added, solvent was removed under vacuum and flask contents were annealed at 140° C. for 19 h. Then SSP was restarted for 47 h at 180° C. under same vacuum. NMR of the polymer was monitored over time until desired Mn was achieved. At this point, the mass obtained was recorded and used for yield calculation (77.3%).

A portion of the material was sent out for PIXE (Proton Induced X-ray Emission analysis) to characterize metal/elements contents and for GPC (gel permeation chromatography) to characterize Mn (number average molecular weight). The remaining of the material was analyzed by UV absorbance at 5 mg/ml polymer concentration in hexafluoroisopropanol at 400 nm.

Example 2

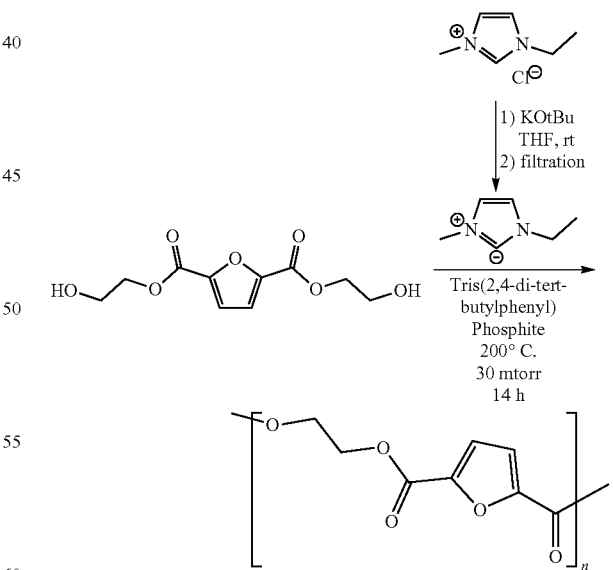

Inside an Argon-charged glove bag, 1-ethyl-3-methyl imidazolium chloride (0.051 eq), sublimed potassium tert-butoxide (0.06 eq) and anhydrous THF (0.034 M with imidazolium precursor) were added to a 3 neck flame dried round bottom flask equipped with a stir bar. Then this reaction mixture was taken out of the glove bag and put under inert gas while being stirred for 20 min at 25° C. Then this mixture was moved back inside the Argon-charged glove bag and it was filtered through a 0.45 μm filter into a flame-dried 3 neck round bottom flask equipped with a stir bar and containing bis(2-hydroxyethyl) furan-2,5-dicarboxylate (1 eq) and Tris(2,4-di-tert-butylphenyl) Phosphite (0.35 mol %). This reaction flask was taken out of the glove bag and stirred for 10 min at 25 C under inert gas until a solid was suspended. Then the THF was vacuumed off slowly to prevent splashing. Once only solids remained, the round bottom flask was immersed in an oil bath at 100° C. and it was heated gradually to 200° C. (oil bath temp) while under vacuum. Once the desired temperature was reached, it was held at this temp for 14 h under vacuum (30-40 mtorr). The reaction flask was then cooled down to room temperature and was moved into an Argon-charged glove bag. The contents of the flask were then scratched off with a spatula (a powder was obtained) and transferred into a flame dried 3 neck round bottom flask and placed on a rotovap at 1 rotation per sec and immersed in an oil bath at 195° C. under vacuum (1 torr) for solid state polymerization (57 h total time). After 40 h of SSP, 0.04 eq of NHC carbene dissolved in THF was added, solvent was removed under vacuum and SSP was restarted for last 17 h. NMR of the polymer was monitored over time until desired Mn was achieved. At this point, the mass obtained was recorded and used for yield calculation (68.3%).

A portion of the material was sent out for PIXE (Proton Induced X-ray Emission analysis) to characterize metal/elements contents and for GPC (gel permeation chromatography) to characterize Mn (number average molecular weight). The remaining of the material was analyzed by UV absorbance at 5 mg/ml polymer concentration in hexafluoroisopropanol at 400 nm.

Example 3

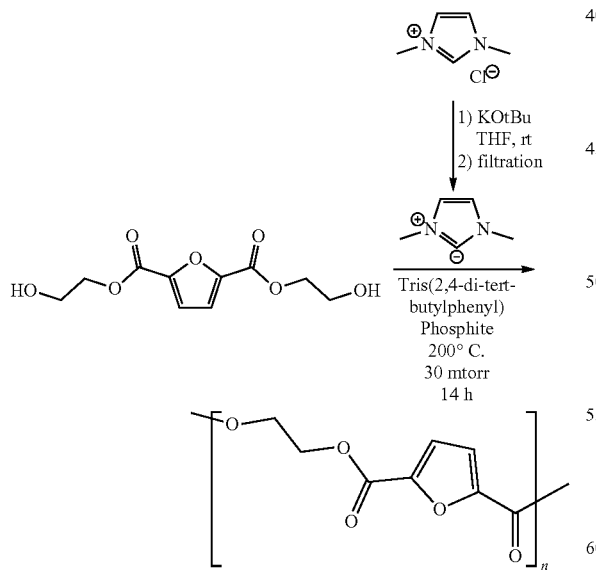

Inside an Argon-charged glove bag, 1,3-dimethylimidazolium chloride (0.08 eq), sublimed potassium tert-butoxide (0.064 eq) and anhydrous THF (0.035 M with imidazolium precursor) were added to a 3 neck flame dried round bottom flask equipped with a stir bar. Then this reaction mixture was taken out of the glove bag and put under inert gas while being stirred for 51 min at 25° C. Then this mixture was moved back inside the Argon-charged glove bag and it was filtered through a 0.45 μm filter into a flame-dried 3 neck round bottom flask equipped with a stir bar and containing bis(2-hydroxyethyl) furan-2,5-dicarboxylate (1 eq) and Tris (2,4-di-tert-butylphenyl) Phosphite (0.335 mol %). This reaction flask was taken out of the glove bag and stirred for 5 min at 25° C. under inert gas until a solid was suspended. Then the THF was vacuumed off slowly to prevent splashing. Once only solids remained, the round bottom flask was immersed in a 140° C. oil bath and it was heated gradually to 230° C. (oil bath temp) while under vacuum. Once the desired temperature was reached, it was held at this temp for 3 h under vacuum (35 mtorr). The reaction flask was then cooled down to room temperature and was moved into an Argon-charged glove bag. The contents of the flask were then dissolved in hexafluoroisopropanol (HFIP) and transferred into a flame dried 3 neck Morton indented flask. Once all HFIP has been removed and contents were completely dried, the flask was heated to 140° C. under vacuum (50 mtorr) for 16 h. The flask was then cooled down to room temperature under vacuum and moved into the Argon-charged glove bag so that the material could be crushed to a powder (<3 mm diameter). The reaction flask was then placed on a rotovap at 1 rotation per sec and immersed in an oil bath at 180° C. under vacuum (2-3 torr) for solid state polymerization (total time: 69 h). NMR of the polymer was monitored over time until desired Mn was achieved. At this point, the mass obtained was recorded and used for yield calculation (79.8%).

A portion of the material was sent out for PIXE (Proton Induced X-ray Emission analysis) to characterize metal/elements contents and for GPC (gel permeation chromatography) to characterize Mn (number average molecular weight). The remaining of the material was analyzed by UV absorbance at 5 mg/ml polymer concentration in hexafluoroisopropanol at 400 nm.

Example 4

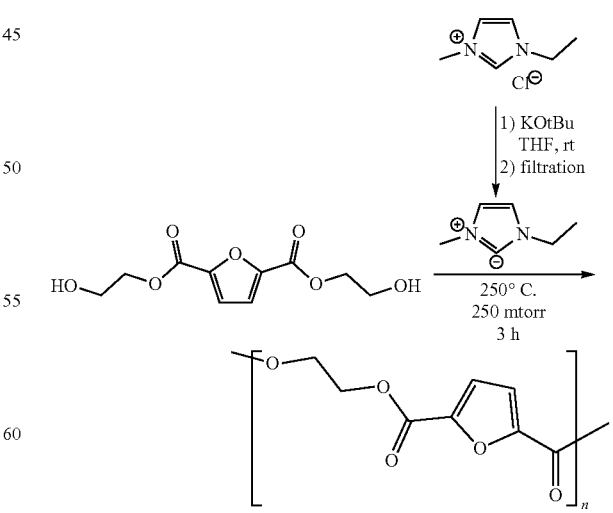

Inside an Argon-charged glove bag, 1,3-dimethylimidazolium chloride (0.072 eq), sublimed potassium tert-butoxide (0.071 eq) and anhydrous THF (0.07 M with imidazolium precursor) were added to a 3 neck flame dried round bottom flask equipped with a stir bar. Then this reaction mixture was taken out of the glove bag and put under inert gas while being stirred for 35 min at 25° C. Then this mixture was moved back inside the Argon-charged glove bag and it was filtered through a 0.45 μm filter into a flame-dried 3 neck round bottom flask equipped with a stir bar and containing bis(2-hydroxyethyl) furan-2,5-dicarboxylate (1 eq). This reaction flask was taken out of the glove bag and stirred for 5 min at 25° C. under inert gas until a solid was suspended. Then the THF was vacuumed off slowly to prevent splashing. Once only solids remained, the round bottom flask was immersed in a 140° C. oil bath and it was heated gradually to 250° C. (oil bath temp) while under vacuum (250 mtorr). Once the desired temperature was reached, it was held at this temp for 3 h under vacuum. Then it was cooled to 140° C. and left at this temperature while under vacuum for 16 h. The reaction flask was then cooled down to room temperature and was moved into an Argon-charged glove bag. The contents of the flask were then dissolved in hexafluoroisopropanol (HFIP) and transferred into a flame dried 3 neck Morton indented flask. Once all HFIP has been removed and contents were completely dried, the flask was moved back into the Argon-charged glove bag so that the material could be crushed to a powder (<3 mm diameter). The reaction flask was then placed on a rotovap at 1 rotation per sec and immersed in an oil bath at 140° C. which was raised to 180° C. for solid state polymerization under vacuum at 3-4 torr (total time 100 h). NMR of the polymer was monitored over time until desired Mn was achieved. At this point, the mass obtained was recorded and used for yield calculation (85.8%).

A portion of the material was sent out for PIXE (Proton Induced X-ray Emission analysis) to characterize metal/elements contents and for GPC (gel permeation chromatography) to characterize Mn (number average molecular weight). The remaining of the material was analyzed by UV absorbance at 5 mg/ml polymer concentration in hexafluoroisopropanol at 400 nm.

Example 5

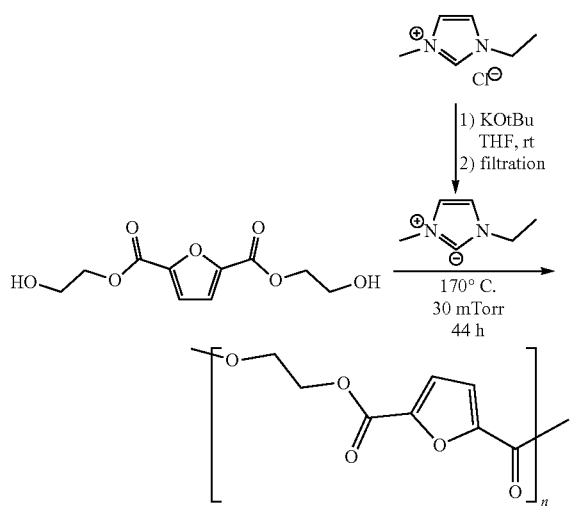

Inside an Argon-charged glove bag, 1-ethyl-3-methyl imidazolium chloride (0.051 eq), sublimed potassium tert-butoxide (0.06 eq) and anhydrous THF (0.034 M with imidazolium precursor) were added to a 3-neck flame dried round bottom flask equipped with a stir bar. Then this reaction mixture was taken out of the glove bag and put under inert gas while being stirred for 20 min at 25° C. Then this mixture was moved back inside the Argon-charged glove bag and it was filtered through a 0.45 μm filter into a flame-dried 3 neck round bottom flask equipped with a stir bar and containing bis(2-hydroxyethyl) furan-2,5-dicarboxylate (1 eq). This reaction flask was taken out of the glove bag and stirred for 10 min at 25° C. under inert gas until a solid was suspended. Then the THF was vacuumed off slowly to prevent splashing. Once only solids remained, the round bottom flask was immersed in an oil bath at room temperature and it was heated gradually to 170° C. (oil bath temp) while under vacuum. Once the desired temperature was reached, it was held at this temp for 44 h under vacuum (30 mtorr). The reaction flask was then cooled down to room temperature and was moved into an Argon-charged glove bag. At this point, the mass obtained was recorded and used for yield calculation (81.8%).

A portion of the material was sent out for GPC (gel permeation chromatography) to characterize Mn (number average molecular weight). UV absorbance of this material was obtained at 5 mg/ml solution in hexafluoroisopropanol (HFIP) at 400 nm.

TABLE 1

Summary of reaction conditions for polymerization

| Expt No. | Polymerization oil bath temperature (° C.) | Polymerization time (h) | NHC imidazolium precursor catalyst | antioxidant |
|---|---|---|---|---|
| 1 | 170 | 44 | 1-ethyl-3-methyl imidazolium chloride | Tris(2,4-di-tert-butylphenyl) Phosphite |
| 2 | 200 | 14 | 1-ethyl-3-methyl imidazolium chloride | Tris(2,4-di-tert-butylphenyl) Phosphite |
| 3 | 230 | 3 | 1,3-dimethylimidazolium chloride | Tris(2,4-di-tert-butylphenyl) Phosphite |
| 4 | 250 | 3 | 1,3-dimethylimidazolium chloride | none |
| 5 | 170 | 44 | 1-ethyl-3-methyl imidazolium chloride | none |

TABLE 2

Summary of solid state polymerization conditions

| Experiments | Annealing at 140° C. | Annealing time (h) | Solid state polymerization temp (° C.) | Solid state polymerization time (hours) |
|---|---|---|---|---|
| 1* | Yes | 21 | 180 | 131 |
| 2** | No | N/A | 180-195 | 57 |
| 3 | Yes | 16 | 180 | 69 |
| 4 | Yes | 16 | 180 | 100 |

*polymer was annealed after 3.5 days of SSP. More NHC catalyst (0.04 eq) was added before annealing.
**NHC catalyst (0.04 eq) was added after x days of SSP. 40 h SSP at 195° C. and 17 h SSP at 180° C.

TABLE 3

Summary of yield, Mn, Mw and UV absorbance

| Expt No. | Polymerization oil bath temperature (° C.) | Yield post SSP (%) | Mn pre SSP * (Da) | Mn post SSP** (Da) | Mw post SSP** (Da) | UV absorbance at 400 nm *** post SSP (no precipitation) |
|---|---|---|---|---|---|---|
| 1 | 170 | 77.3 | 2577 | 10075 | 26781 | 0.0819 |
| 2 | 200 | 68.3 | 6775 | 13602 | 34909 | 0.1948 |
| 3 | 230 | 79.8 | 14710 | 18480 | 57319 | 0.4659 |
| 4 | 250 | 85.8 | 5750 | 17525 | 147868 | 1.6189 |

\* calculated by NMR.
\*\*measured by GPC.
\*\*\* 5 mg/ml of PEF in hexafluoroisoproanol

TABLE 4

Summary of GPC data (calculated from the refractive index detector signal relative to calibration curve of PMMA standards)

| Experiment | Vp$^a$ | Mn (Da) | Mw (Da) | Mz (Da) | PDI$^b$ |
|---|---|---|---|---|---|
| 1 | 28.07 | 10075 | 26781 | 56840 | 2.658 |
| 2 | 26.95 | 13602 | 34909 | 68360 | 2.566 |
| 3 | 26.12 | 18480 | 57319 | 132743 | 3.102 |
| 4 | 27.01 | 17525 | 147868 | 743086 | 8.437 |

$^a$Vp = peak retention volume.
$^b$PDI = polydispersity

The data in Tables 3 and 4 demonstrates that high Mn and Mw can be achieved using carbene as catalyst and SSP techniques, and that the temperature of the polymerization is increased, the color of the PEF increases.

TABLE 5

Data comparison between PEFs synthesized with and without antioxidant

| Expt No. | Antioxidant | Mn pre SSP* (Da) | UV at 400 nm pre SSP* (no precipitation) |
|---|---|---|---|
| 1 | yes | 2577 | 0.037 |
| 5 | no | 2065 | 0.099 |

*5 mg/ml of PEF in hexafluoroisoproanol

The data in Table 5 demonstrates that low color content of PEF can be achieved and that using an antioxidant in the polymerization decrease the PEF color post polymerization.

TABLE 6

PIXE analysis of PEF

| Elements | Elements mass fraction (%) in PEF from prior art* | Average Elements mass fraction (%) in PEF from examples 1-4. (data shown as <0.0X% means it was undetected and is less than the detection limit of the PIXE instrument) |
|---|---|---|
| Sn | 0.0261 | <0.001977 |
| Ti | 0.0105 | <0.0003115 |
| Zr | 0.0801 | <0.0002332 |
| Hf | 0.1567 | <0.0001143 |
| Bi | 0.1834 | <0.0001518 |
| Pb | 0.1818 | <0.0001602 |
| Mo | 0.0843 | <0.0002636 |
| Ga | 0.0613 | <0.000034 |

TABLE 6-continued

PIXE analysis of PEF

| Elements | Elements mass fraction (%) in PEF from prior art* | Average Elements mass fraction (%) in PEF from examples 1-4. (data shown as <0.0X% means it was undetected and is less than the detection limit of the PIXE instrument) |
|---|---|---|
| Zn | 0.0574 | 0.002048 |
| Ho | 0.1448 | <0.0001286 |
| Tb | 0.1395 | <0.0003676 |
| Yb | 0.1519 | <0.0001713 |
| Dy | 0.1427 | <0.0004035 |
| Nd | 0.1266 | <0.0004754 |
| Co | 0.0518 | <0.0000732 |
| Fe | 0.0491 | 0.0032 |
| Sm | 0.1320 | <0.0002542 |
| Er | 0.1468 | <0.0002063 |
| Pr | 0.1237 | <0.0006628 |
| Eu | 0.1334 | <0.0002676 |
| V | 0.0448 | <0.0002057 |
| Y | 0.0781 | <0.0001821 |
| Sb | 0.1069 | <0.005409 |
| Gd | 0.1381 | <0.0001910 |
| La | 0.1220 | <0.0008725 |
| Sc | 0.0395 | <0.0003514 |
| Cu | 0.0558 | 0.00014 |
| Mg | 0.0214 | 0.014 |
| Mn | 0.0483 | 0.00034 |
| Al | 0.0237 | 0.0075 |
| Ta | 0.1588 | <0.0001257 |
| Ce | 0.1230 | <0.0006927 |
| K | 0.0344 | 0.513 |
| Ge | 0.0638 | <0.00004173 |
| Sr | 0.0770 | <0.0001337 |
| Ca | 0.0352 | 0.0085 |
| Nb | 0.0816 | <0.0002848 |
| Cr | 0.0457 | 0.00057 |
| Li | 0.0061 | Not analyzed |
| Pt | 0.1712 | <0.0001898 |
| Ni | 0.0516 | 0.00021 |
| In | 0.1008 | <0.001709 |

*From Tables 4, 5 and 6 from this reference: Gruter, G-J. M.; Sipos, L.; Dam, M. A. *Combinatorial Chemistry & High Throughput Screening*, 2012, 15, 180-188.

TABLE 7

Elemental analysis of C, H and N in the PEF synthesized in example 2

| Elements | Elements mass % in PEF |
|---|---|
| C | 49.19 |
| H | 3.28 |
| N | 0.20 |

The data in Table 7 demonstrates that the presence of NHC catalyst residue in the PEF synthesized in accordance with the present application. The nitrogen content comes from the NHC carbene residue in the polymer composition.

What is claimed is:

1. A polymer composition having reduced color content, comprising:
    a polymer with a polymer backbone, wherein the polymer backbone comprises one of a substituted or unsubstituted f urandicarboxylate moiety and a substituted or unsubstituted tetrahydrof urandicarboxylate moiety, and
    an organocatalyst comprising carbene, or a fragment of the organocatalyst thereof,
    wherein the composition is free from metal catalysts or metal catalyst fragments, wherein the metal catalysts are at least one of a transesterification catalyst, a polycondensation catalyst, or polymerization catalysts used to produce the polymer or precursors thereof, and wherein the polymer composition having a reduced color content has a number average molecular weight of at least 10,000 Da, and wherein a solution of 5 mg/mL of the composition in (i) hexafluoroisopropanol or (ii) hexafluoroisopropanol/dichloromethane has an absorbance of less than 0.5 at 400 nm.

2. The polymer composition of claim 1, wherein the solution of 5 mg/mL of the polymer composition in (i) hexafluoroisopropanol or (ii) hexafluoroisopropanol/dichloromethane has an absorbance of less than 0.08 to 400 nm.

3. The polymer composition of claim 1, wherein the solution of 5 mg/mL of the polymer composition in (i) hexafluoroisopropanol or (ii) hexafluoroisopropanol/dichloromethane has an absorbance of less than 0.05 to 400 nm.

4. The polymer composition of claim 1, wherein the organocatalyst is an N-heterocyclic carbene.

5. The polymer composition of claim 1, wherein the substituted or unsubstituted furandicarboxylate moiety is the substituted or unsubstituted 2,5-furandicarboxylate moiety, and the substituted or unsubstituted tetrahydrofurandicarboxylate moiety is the substituted or unsubstituted 2,5-tetrahydrofurandicarboxylate moiety.

6. The polymer composition of claim 1, wherein the substituted or unsubstituted furandicarboxylate moiety is:

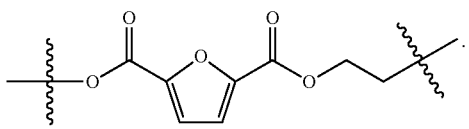 [SMILES: *CCOC(=O)c1ccc(C(=O)O*)o1]

7. The polymer composition of claim 1, wherein the polymer is poly(alkylene-2,5-furandicarboxylate) or poly(alkylene-2,5-tetrahydrofurandicarboxylate).

8. The polymer composition of claim 1, wherein the polymer is poly-ethylene-2,5-furandicarboxylate) or poly(ethylene-2,5-tetrahydrofurandicarboxylate).

9. The polymer composition of claim 1, wherein the polymer is poly-ethylene-2,5-furandicarboxylate) (PEF), and wherein the organocatalyst is a N-heterocyclic carbene.

10. The polymer composition of claim 1, further comprising an antioxidant or fragment thereof.

11. The polymer composition of claim 1, wherein the composition has a total metal content of less than 0.003 wt %.

12. The polymer composition of claim 1, wherein the composition has less than 0.005 wt % of antimony.

13. The polymer composition of claim 1, wherein the composition has a total content of aluminum, titanium, vanadium, chromium, manganese, iron, cobalt, zinc, germanium, zirconium, cadmium, tin, antimony, hafnium, tungsten, lead, and bismuth, if present, less than 0.02 wt % combined.

14. The polymer composition of claim 1, wherein the total metal content includes the content of transition metals, post-transition metals, metalloids, or lanthanoid metals, or any combinations thereof.

15. A method of preparing a polymer composition having reduced color content, comprising:

a) polymerizing one of a substituted or unsubstituted furan-2,5-dicarboxylic acid dialkyl ester, and a substituted or unsubstituted tetrahydrofuran-2,5-dicarboxylic acid dialkyl ester in the presence of an organocatalyst and an antioxidant at a temperature of less than 250° C.; and b) annealing the polymer composition, followed by performing solid state polymerization to provide a polymer composition having reduced color content, wherein the polymer composition comprises one of the substituted or unsubstituted furandicarboxylate moiety and the substituted or unsubstituted tetrahydrofurandicarbwrylate moiety, and an organocatalyst comprising carbene, or a fragment of the organocatalyst thereof, wherein the polymer composition is free from metal catalysts or metal catalyst fragments, wherein the metal catalysts are at least one of a transesterification catalyst, a polycondensation catalyst, or polymerization catalysts used to produce the polymer or precursors thereof, and wherein a solution of 5 mg/mL of the polymer composition in (i) hexafluoroisopropanol or (ii) hexafluoroisopropanol/dichloromethane has an absorbance of less than 0.5 at 400 nm; and wherein the polymer composition having reduced color content has a number average molecular weight of at least 10,000 Da.

16. The method of claim 15, wherein in step a), the temperature is less than 230° C.

17. The method of claim 15, wherein in step a), the temperature is less than 200° C.

18. The method of claim 15, wherein in step a), the temperature is less than 170° C.

19. The method of claim 15, wherein the solution of 5 mg/mL of the polymer composition in (i) hexafluoroisopropanol or (ii) hexafluoroisopropanol/dichloromethane has an absorbance of less than 0.08 to 400 nm.

20. The method of claim 15, wherein the solution of 5 mg/mL of the polymer composition in (i) hexafluoroisopropanol or (ii) hexafluoroisopropanol/dichloromethane has an absorbance of less than 0.05 at 400 nm.

21. The method of claim 15, wherein the organocatalyst is an N-heterocyclic carbene.

22. A polymer composition having reduced color content produced by the method according to claim 15.

* * * * *